(12) United States Patent
Shitagaki et al.

(10) Patent No.: US 8,231,984 B2
(45) Date of Patent: Jul. 31, 2012

(54) QUINOXALINE DERIVATIVE, AND ORGANIC SEMICONDUCTOR DEVICE, ELECTRIC FIELD LIGHT EMITTING DEVICE, AND ELECTRONIC DEVICE WHICH HAVE THE SAME

(75) Inventors: Satoko Shitagaki, Kanagawa (JP); Atsushi Tokuda, Kanagawa (JP); Hiroko Abe, Tokyo (JP); Ryoji Nomura, Kanagawa (JP); Satoshi Seo, Kanagawa (JP)

(73) Assignee: Semiconductor Energy Laboratory Co., Ltd. (JP)

( * ) Notice: Subject to any disclaimer, the term of this patent is extended or adjusted under 35 U.S.C. 154(b) by 0 days.

(21) Appl. No.: 12/557,687

(22) Filed: Sep. 11, 2009

(65) Prior Publication Data

US 2010/0069636 A1    Mar. 18, 2010

Related U.S. Application Data

(62) Division of application No. 10/826,838, filed on Apr. 16, 2004, now Pat. No. 7,601,435.

(30) Foreign Application Priority Data

Apr. 18, 2003  (JP) .................................. 2003-115102
Aug. 27, 2003  (JP) .................................. 2003-302998

(51) Int. Cl.
*B32B 9/00*  (2006.01)
*C07D 241/36*  (2006.01)

(52) U.S. Cl. ........ 428/690; 428/917; 544/349; 544/350; 544/356; 313/504; 313/506; 257/E51.05; 257/E51.051

(58) Field of Classification Search ........................ None
See application file for complete search history.

(56) References Cited

U.S. PATENT DOCUMENTS 4,760,006 A    7/1988 Pawlowski
(Continued)

FOREIGN PATENT DOCUMENTS

EP    0 166 230 A1    1/1986
(Continued)

OTHER PUBLICATIONS

Delvigs, P., "Effects of Multifunctional Crosslinking Agents on the Thermomechanical Properties of Polyimide Films," Polymer Engineering and Science, vol. 16, No. 5, May 1976, pp. 323-326.

(Continued)

*Primary Examiner* — Jill Gray
(74) *Attorney, Agent, or Firm* — Husch Blackwell LLP

(57) ABSTRACT

Target is to provide an organic compound material having a bipolar character.
A quinoxaline derivative represented by a general formula (1) is provided. In the formula, $R^1$-$R^{12}$ each independently represents a hydrogen atom, a halogen atom, a lower alkyl group, an alkoxy group, an acyl group, a nitro group, a cyano group, an amino group, a dialkylamino group, a diarylamino group, a vinyl group, an aryl group, or a heterocyclic residue group. $R^9$ and $R^{10}$, $R^{10}$ and $R^{11}$, and $R^{11}$ and $R^{12}$ are each independent or respectively mutually bonded to form an aromatic ring. $Ar^1$-$Ar^4$ each independently represents an aryl group or a heterocyclic residue group. $Ar^1$, $Ar^2$, $Ar^3$ and $Ar^4$ are each independent or $Ar^1$ and $Ar^2$, and $Ar^3$ and $Ar^4$ are respectively mutually bonded directly, or $Ar^1$ and $Ar^3$, and $Ar^3$ and $Ar^4$ are bonded via oxygen (O), sulfur (S) or a carbonyl group.

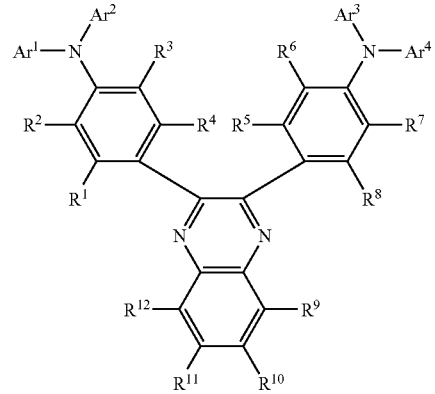

11 Claims, 19 Drawing Sheets

U.S. PATENT DOCUMENTS

| | | | |
|---|---|---|---|
| 5,366,811 | A | 11/1994 | Higashi et al. |
| 5,466,392 | A | 11/1995 | Hironaka et al. |
| 6,303,238 | B1 | 10/2001 | Thompson et al. |
| 6,541,129 | B1 | 4/2003 | Kawamura et al. |
| 6,723,445 | B2 | 4/2004 | Li et al. |
| 7,034,026 | B2 | 4/2006 | Barnett et al. |
| 7,074,534 | B2 | 7/2006 | Herron et al. |
| 7,245,073 | B2 | 7/2007 | Shitagaki et al. |
| 7,399,537 | B2 | 7/2008 | Kawamura et al. |
| 2003/0143430 | A1 | 7/2003 | Kawamura et al. |
| 2005/0065342 | A1 | 3/2005 | Shitagaki et al. |
| 2005/0186446 | A1 | 8/2005 | Shitagaki et al. |
| 2005/0191527 | A1 | 9/2005 | Fujii et al. |
| 2006/0263637 | A1 | 11/2006 | Ohsawa et al. |
| 2008/0241591 | A1 | 10/2008 | Kawamura et al. |

FOREIGN PATENT DOCUMENTS

| | | | |
|---|---|---|---|
| EP | 0 502 202 | A1 | 9/1992 |
| EP | 1 029 909 | A1 | 8/2000 |
| JP | 60-258169 | | 12/1985 |
| JP | 64-57261 | | 3/1989 |
| JP | 7-48385 | | 2/1995 |
| JP | 7-150137 | | 6/1995 |
| JP | 8-73443 | | 3/1996 |
| JP | 10-25473 | | 1/1998 |
| JP | 2000-309566 | | 11/2000 |
| JP | 2003-40873 | | 2/2003 |
| JP | 2006-16384 | | 1/2006 |
| WO | WO 92/05131 | A1 | 4/1992 |
| WO | WO 01/41512 | A1 | 6/2001 |
| WO | WO 2004/094389 | A1 | 4/2004 |
| WO | WO 2004/094389 | A1 | 11/2004 |
| WO | WO 2005/115061 | A1 | 12/2005 |
| WO | WO 2006/049334 | A1 | 5/2006 |

OTHER PUBLICATIONS

Parker, S.P. et al, editors, *McGraw-Hill Dictionary of Chemical Terms*, vol. 3 Rd Ed, 1985, p. 200.

Tang, C.W. et al, "Organic Electroluminescent Diodes," Applied Physics Letters, vol. 51, No. 12, Sep. 21, 1987, pp. 913-915.

Adachi, C. et al, "Electroluminescence in Organic Films with Three-Layer Structure," Japanese Journal of Applied Physics, vol. 27, No. 2, Feb. 1988, pp. L269-L271.

Lewis, R.J., editor, *Hawley's Condensed Chemical Dictionary*, 12$^{th}$ edition, 1993, p. 594.

Jakubke, H-D. et al, editors, *Concise Encyclopedia Chemistry*, 1993, p. 490.

Brock, T. et al, "Synthesis and Characterisation of Porous Particulate Polyimides," J. Mater Chem., vol. 4, No. 2, 1994, pp. 229-236.

International Search Report re application No. PCT/US00/32511, dated Mar. 13, 2001.

Thomas, K.R.J. et al, "Quinoxalines Incorporating Triarylamines: Potential Electroluminescent Materials with Tunable Emission Characteristics," Chem. Mater., vol. 14, No. 6, 2002, pp. 2796-2802.

International Search Report re application No. PCT/JP2004/005022, dated Jun. 15, 2004 (in Japanese).

Written Opinion re application No. PCT/JP2004/005022, dated Jun. 15, 2004 (with partial English translation).

U.S. Appl. No. 10/896,615 (abandoned) to Shitagaki et al, filed Jul. 22, 2004, including specification, claims, abstract and drawings (in Japanese).

Burrows, H.D. et al, "Fluorescence Study of Dehydroabietic Acid-Based Bipolar Arylamine-Quinoxalines," Journal of Fluorescence, vol. 16, No. 2, Mar. 2006, pp. 227-231.

Office Action re European application No. EP 04726312.4, dated Dec. 15, 2009.

U.S. Appl. No. 10/896,015 (abandoned) to Shitagaki et al, filed Jul. 22, 2004, including specification, claims, abstract and drawings (in Japanese).

QUINOXALINE DERIVATIVE, AND ORGANIC SEMICONDUCTOR DEVICE, ELECTRIC FIELD LIGHT EMITTING DEVICE, AND ELECTRONIC DEVICE WHICH HAVE THE SAME

This application is a divisional of application Ser. No. 10/826,838 filed on Apr. 16, 2004 now U.S. Pat. No. 7,601,435.

TECHNICAL FIELD

The present invention relates to a quinoxaline derivative which is an organic compound material, and an organic semiconductor device utilizing the same. It also relates to an electric field light emitting device utilizing the aforementioned quinoxaline derivative.

BACKGROUND OF THE INVENTION

Organic compounds include more varied material systems in comparison with inorganic compounds, and have possibility that materials of various functions can be synthesized by an appropriate molecular design. Also they have features that a molded article such as a film is flexible and provides an excellent workability by a polymer formation. Based on these advantages, photonics and electronics utilizing functional organic materials are attracting attention recently.

Examples of an electronic device utilizing an organic compound material as a functional organic material include a solar cell, an electric field light emitting device, and an organic transistor. These are devices utilizing electrophysical properties (carrier transporting property) and optophysical properties (light absorption or emission) of the organic compound material, and, among these, the electric field light emitting device is showing a remarkable progress.

As a most basic device structure of the electric field light emitting device, there is known a structure in which a thin film of a total thickness of about 100 nm, formed by a hole transporting layer constituted of a hole transporting organic compound and an electron transporting light-emitting layer constituted of an electron transporting organic compound, is sandwiched between electrodes (for example cf. non-patent reference 1). By applying a voltage on such device, a light emission can be obtained from the electron transporting organic compound which also has a light emitting property. Such structure is generally called a single hetero (SH) structure.

The electric field light emitting device in the non-patent reference 1 can be considered to be based on a functional separation, namely the transportation of holes being executed by the hole transport layer and the transportation of electrons being executed by the electron transport layer.

Thereafter, for the purposes of further improvement in a change of an emission spectrum and a decrease in the light emission efficiency resulting from an interaction (for example formation of an exciplex) at an interface of the laminated layer, the concept of such functional separation has been developed into a double hetero (DH) structure in which a light emitting layer is inserted between the hole transport layer and the electron transport layer (for example cf. non-patent reference 2).

In an electric field light emitting device as described in the non-patent reference 2, in order to further suppress an interaction generated at the interface, it is preferable to form the light emitting layer with a bipolar material having both the electron transporting property and the hole transporting property.

However, organic compound materials are mostly a monopolar material, having either the hole transporting property or the electron transporting property. For example, a material shown in the following patent reference 1 is only applied as an electron injecting layer.

It is therefore desired to newly develop an organic compound material having a bipolar character.

Patent reference 1: JP-A-2003-40873

Non-patent reference 1: C. W. Tang and one another, Applied Physics Letters, Vol. 51, No. 12, 913-915 (1987)

Non-patent reference 2: Chihaya Adachi and three others, Japanese Journal of Applied Physics, Vol. 27, No. 2, L269-L271 (1988).

SUMMARY OF THE INVENTION

A target of the present invention is to provide an organic compound material having a bipolar property and also a light emitting property. It is also a target to provide an organic semiconductor device utilizing such organic compound material, particularly an electric field light emitting device capable of reducing a device failure such as a dielectric breakdown or improving a light emitting property by employing the aforementioned organic compound material.

MEANS FOR SOLVING THE PROBLEMS

The present invention provides a quinoxaline derivative represented by a general formula (1).

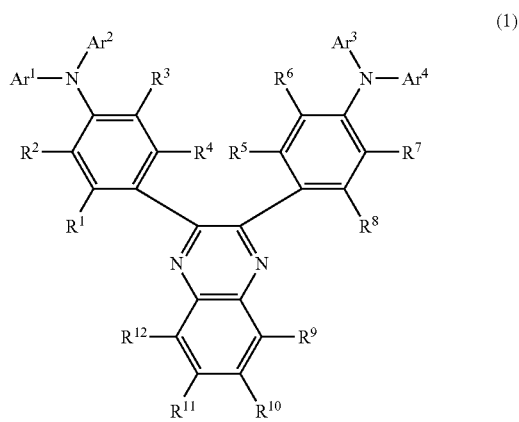

In the formula (1), $R^1$-$R^{12}$ may be same or different and each represents a hydrogen atom, a halogen atom, a lower alkyl group, an alkoxy group, an acyl group, a nitro group, a cyano group, an amino group, a dialkylamino group, a diarylamino group, a vinyl group that may have a substituent, an aryl group that may have a substituent, or a heterocyclic residue group that may have a substituent. Also, $R^9$ and $R^{10}$, $R^{10}$ and $R^{11}$, or $R^{11}$ and $R^{12}$ may be mutually bonded to form an aromatic ring. Also $Ar^1$-$Ar^4$ may be same or different and each represents an aryl group that may have a substituent or a heterocyclic residue group that may have a substituent. Also $Ar^1$ and $Ar^2$, and $Ar^3$ and $Ar^4$ may be mutually bonded directly as shown in a following general formula (68), or bonded via oxygen (O), sulfur (S) or a carbonyl group as shown in a following general formula (69).

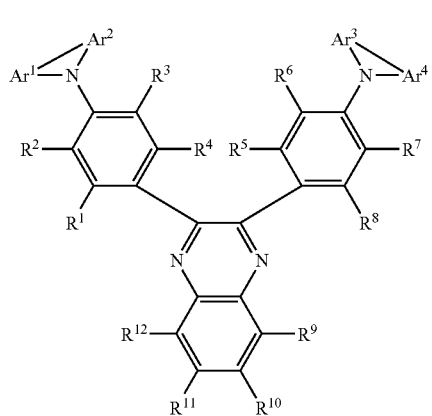
(68)

In the formula (68), $R^1$ to $R^{12}$ are same as shown in the formula (1).

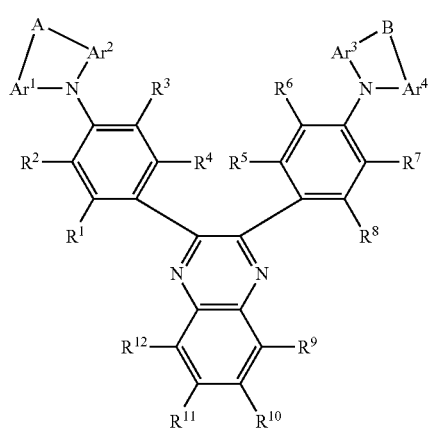
(69)

In the formula (69), A and B represent oxygen (O), sulfur (S), or a carbonyl group. Also $R^1$ to $R^{12}$ are same as shown in the formula (1).

The present invention provides a quinoxaline derivative represented by a general formula (2).

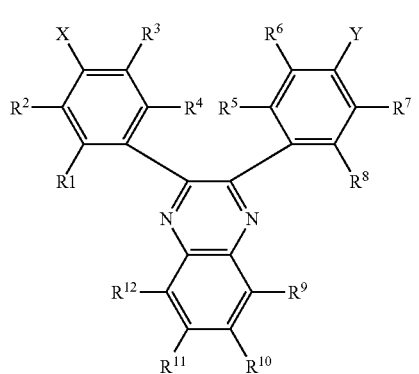
(2)

In the formula (2), X and Y each is represented by either one of formulas (3)-(5).

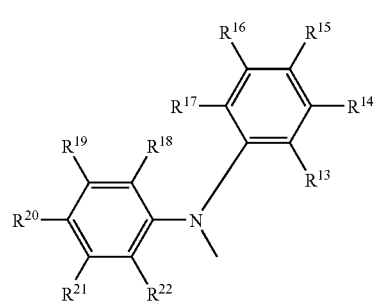
(3)

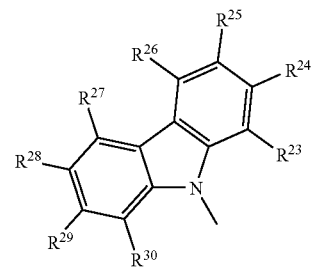
(4)

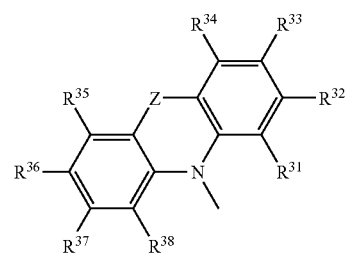
(5)

In the formulas, $R^1$-$R^{38}$ may be same or different and each represents a hydrogen atom, a halogen atom, a lower alkyl group, an alkoxy group, an acyl group, a nitro group, a cyano group, an amino group, a dialkylamino group, a diarylamino group, a vinyl group that may have a substituent, an aryl group that may have a substituent, or a heterocyclic residue group that may have a substituent. Also, $R^9$ and $R^{10}$, $R^{10}$ and $R^{11}$, or $R^{11}$ and $R^{12}$ may be mutually bonded to form an aromatic ring. Z represents oxygen (O), sulfur (S) or a carbonyl group.

The present invention provides a quinoxaline derivative represented by a general formula (6).

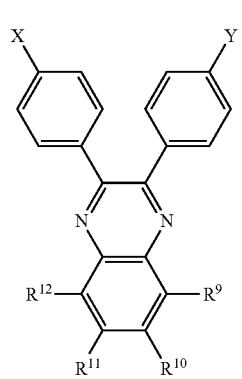
(6)

In the formula (6), X and Y each is represented by either one of formulas (7)-(9).

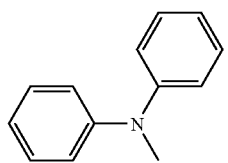
(7)

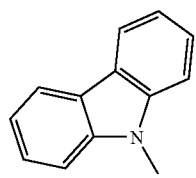
(8)

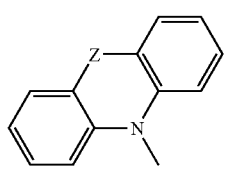
(9)

In the formulas, $R^9$-$R^{12}$ may be same or different and each represents a hydrogen atom, a halogen atom, a lower alkyl group, an alkoxy group, an acyl group, a nitro group, a cyano group, an amino group, a dialkylamino group, a diarylamino group, a vinyl group that may have a substituent, an aryl group that may have a substituent, or a heterocyclic residue group that may have a substituent. Also, $R^9$ and $R^{10}$, $R^{10}$ and $R^{11}$, or $R^{11}$ and $R^{12}$ may be mutually bonded to form an aromatic ring. Z represents oxygen (O), sulfur (S) or a carbonyl group.

In the foregoing general formulas (1), (2) and (6), the lower alkyl group can be a methyl group, an ethyl group, an n-propyl group, an isopropyl group, an n-butyl group, a sec-butyl group, a tert-butyl group, or a hexyl group and preferably includes 1-6 carbon atoms. It can also be a halogenated alkyl group such as a trifluoromethyl group, or a cycloalkyl group such as a cyclohexyl group. The alkoxy group can be a methoxy group, an ethoxy group, an n-propoxy group, an isopropoxy group, an n-butoxy group, a sec-butoxy group, a tert-butoxy group or a hexoxy group, and preferably includes 1-6 carbon atoms. The acyl group can be an acetyl group or the like. The dialkylamino group can be a dimethylamino group, a diethylamino group or the like, preferably containing 1-4 carbon atoms in the alkyl chain. The diarylamino group can be a diphenylamino group, a bis($\alpha$-naphthyl)amino group or the like, and also be a substituted arylamino group such as a bis(m-tolyl)amino group. The vinyl group may also be a vinyl group having a substituent such as a diphenylvinyl group. The aryl group can be not only a non-substituted aryl group such as a phenyl group or a naphthyl group, but also a substituted aryl group such as an o-tolyl group, an m-tolyl group, a p-tolyl group, a xylyl group, a methoxyphenyl group, an ethoxyphenyl group or a fluorophenyl group. The heterocyclic residue group can be a pyridyl group, a furyl group, a thienyl group or the like, which may further have a substituent such as a methyl group.

In the following, specific structural formulas of the quinoxaline derivative of the present invention are listed, but the present invention is not limited to these.

[formulas] (10) - (67)

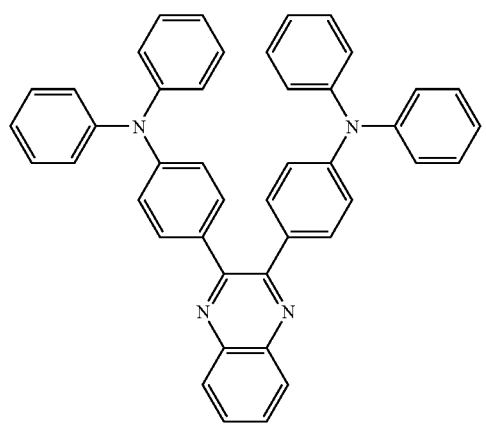
(10)

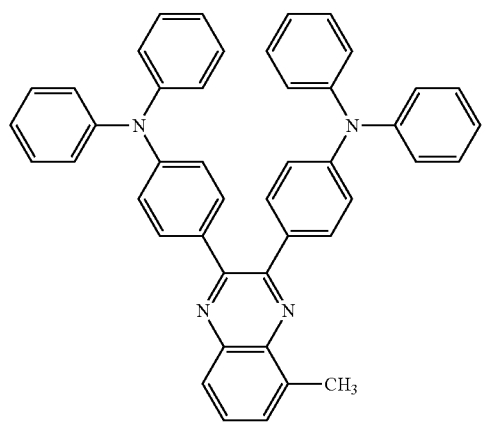
(11)

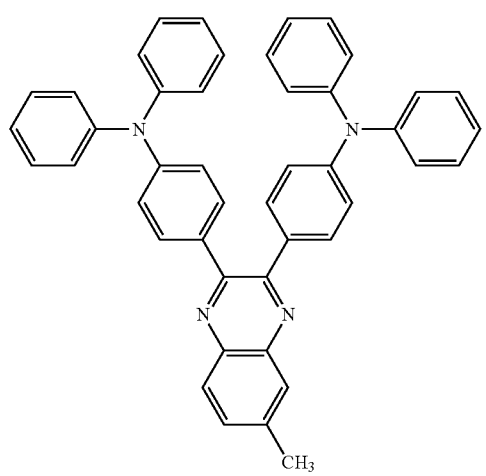
(12)

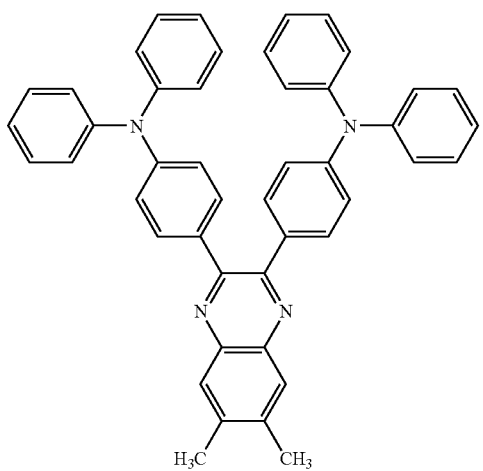
(13)
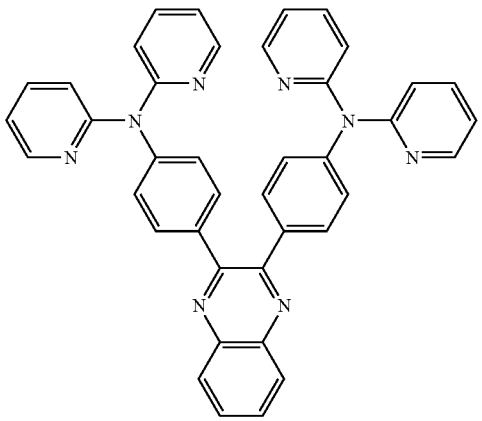
(16)
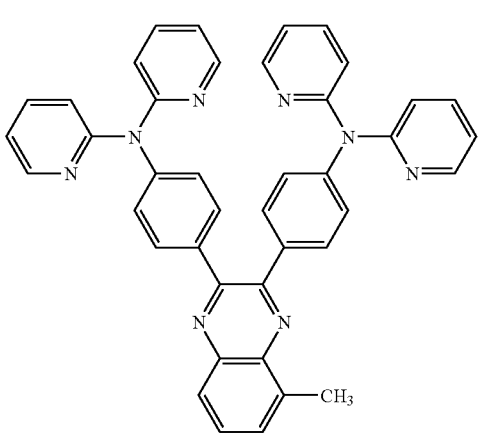
(14)
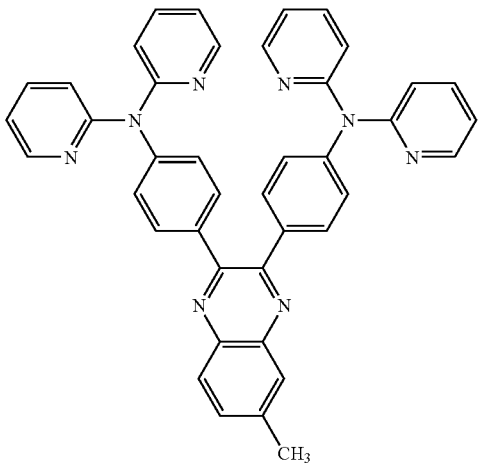
(17)
(15)
(18)

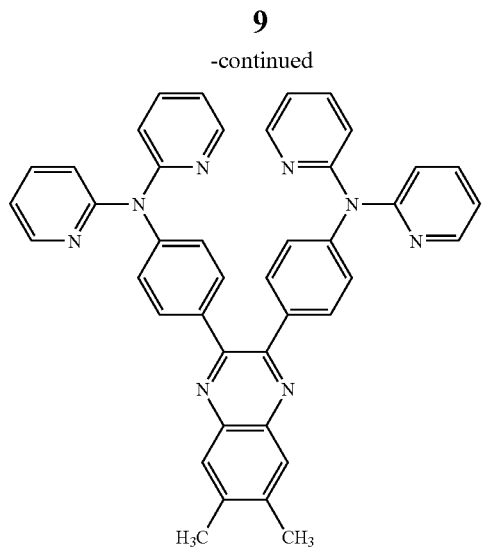
(19)
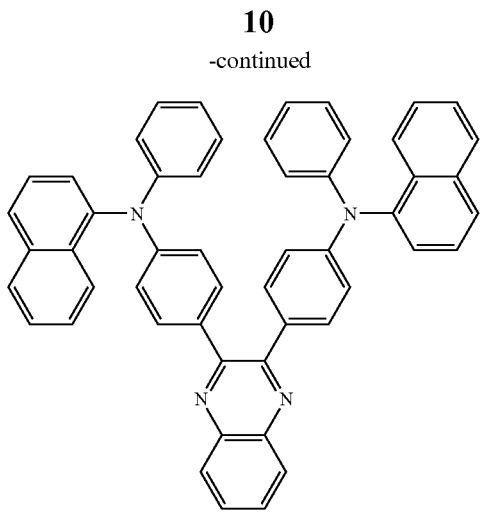
(22)
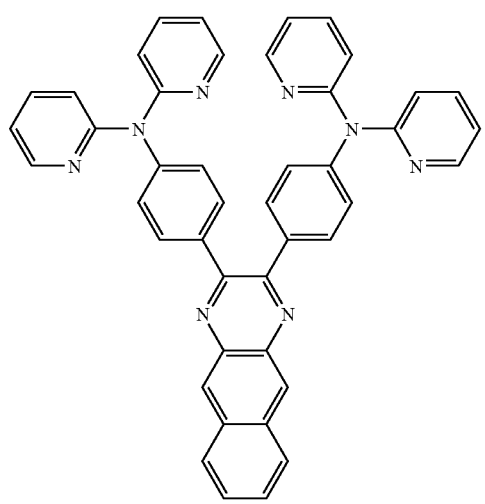
(20)
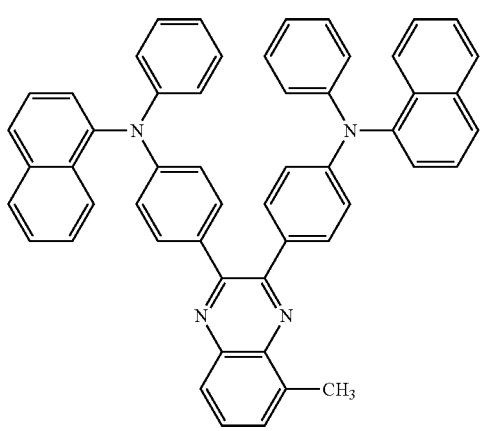
(23)
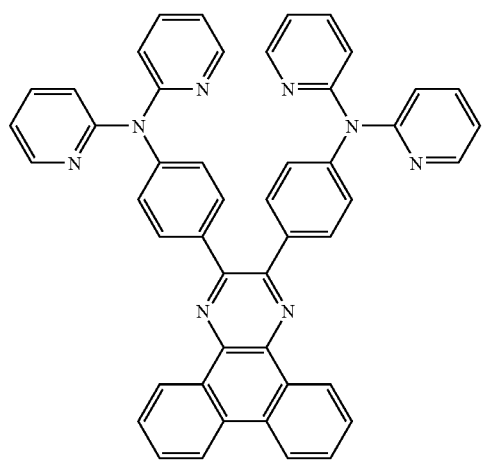
(21)
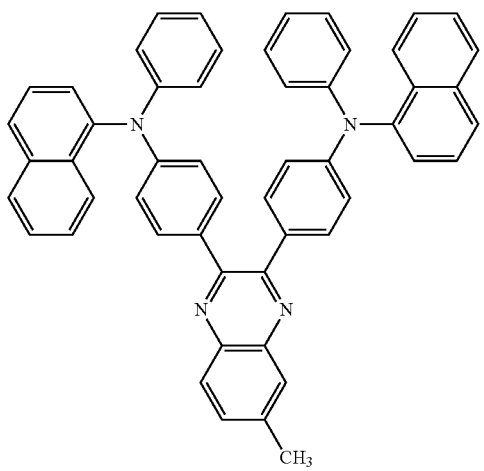
(24)

-continued
(25)
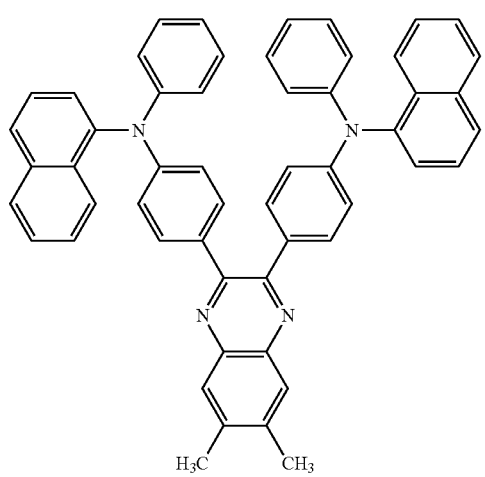
(28)
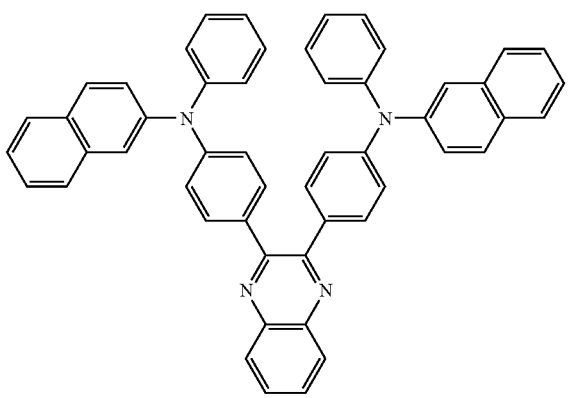
(26)
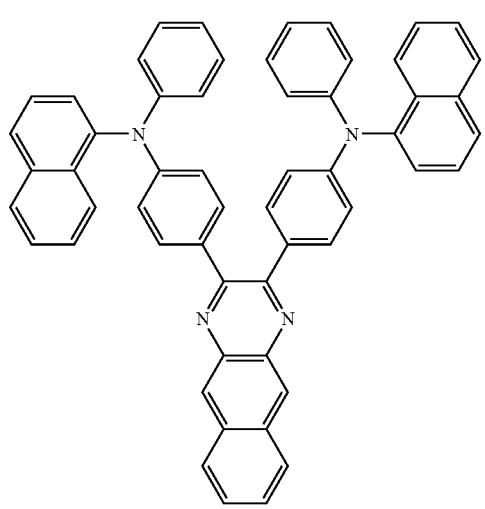
(29)
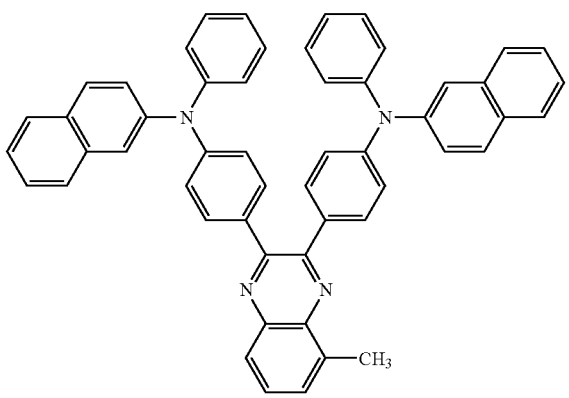
(27)
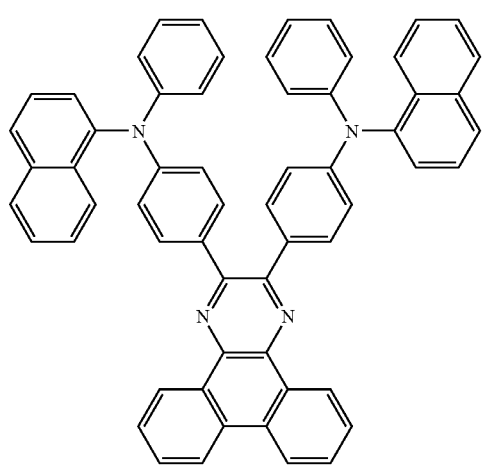
(30)
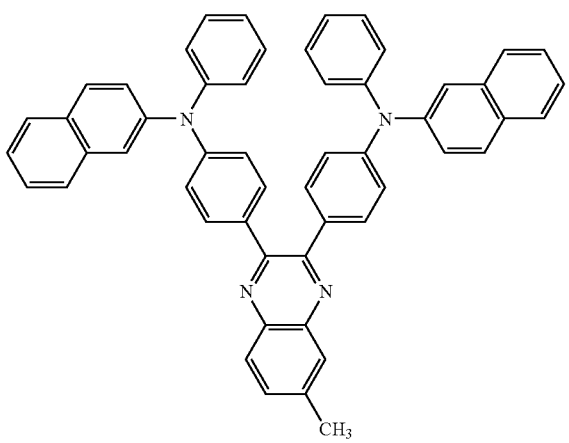

(31)
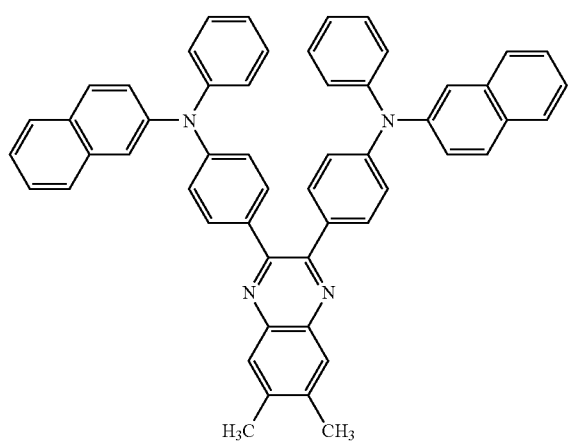
(34)
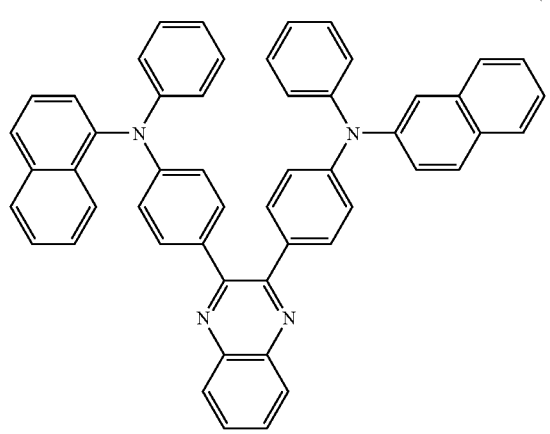
(32)
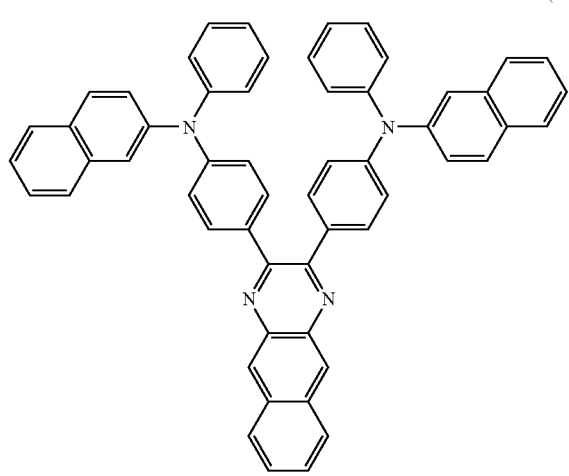
(35)
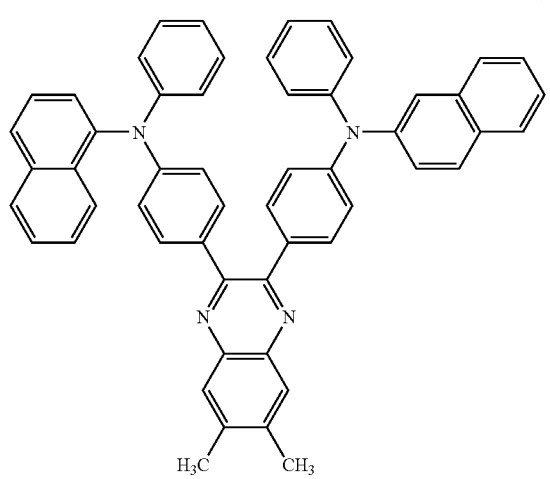
(33)
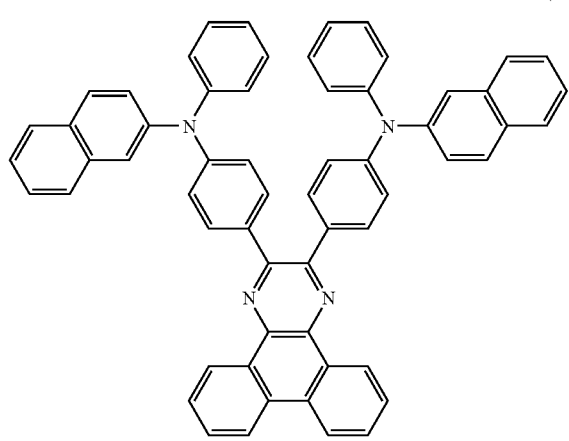
(36)
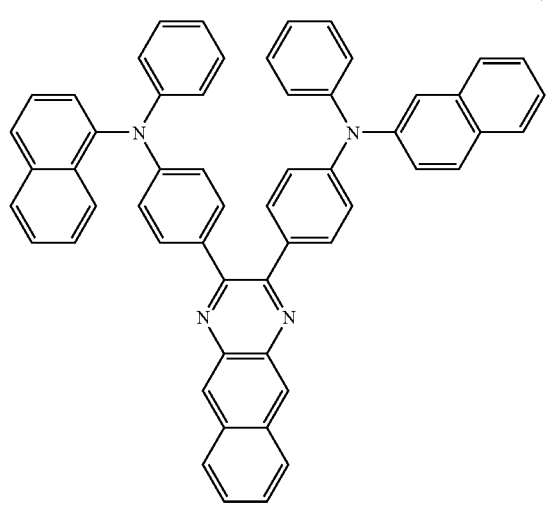

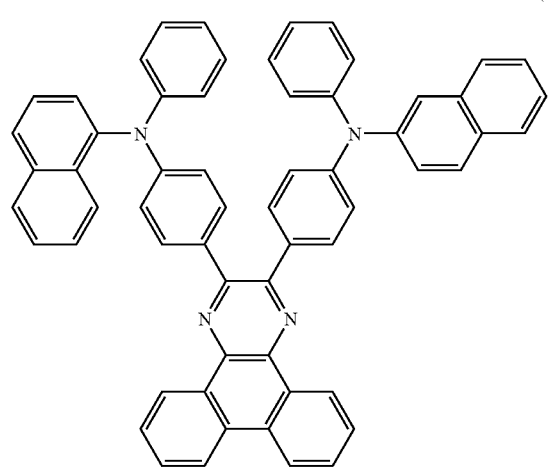
(37)
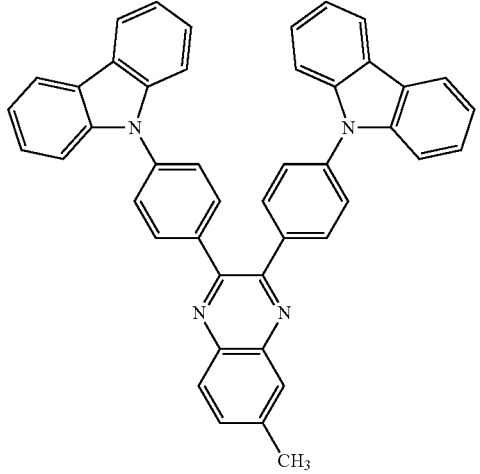
(40)
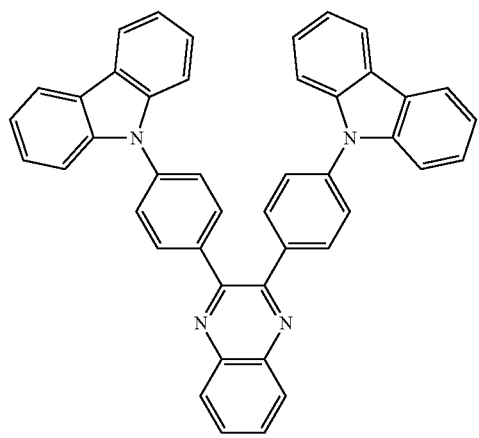
(38)
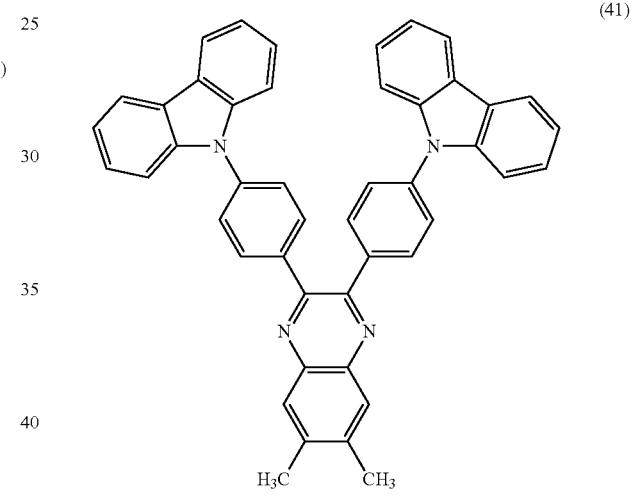
(41)
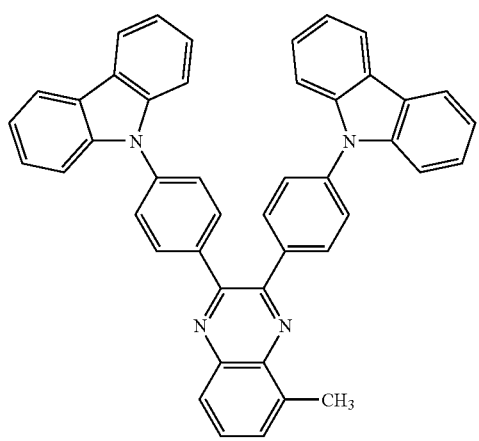
(39)
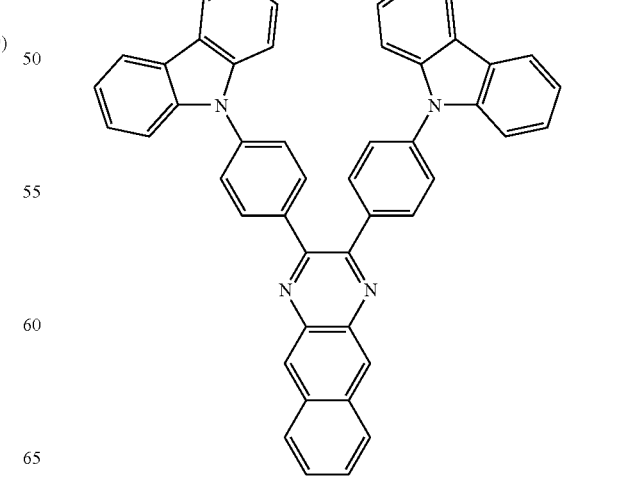
(42)

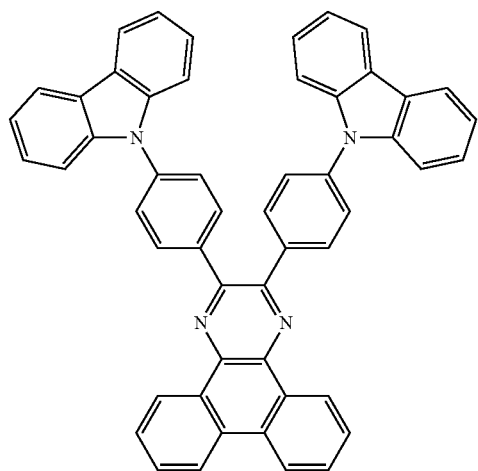
(43)
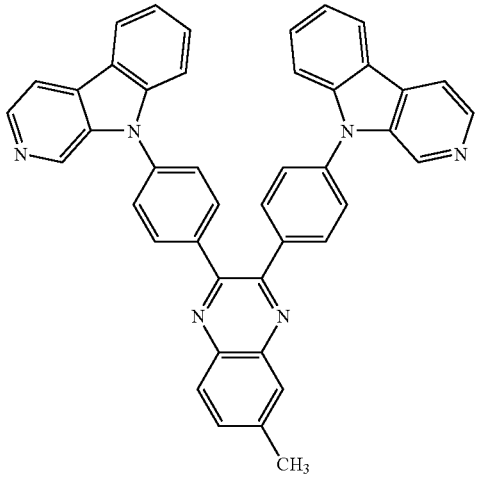
(46)
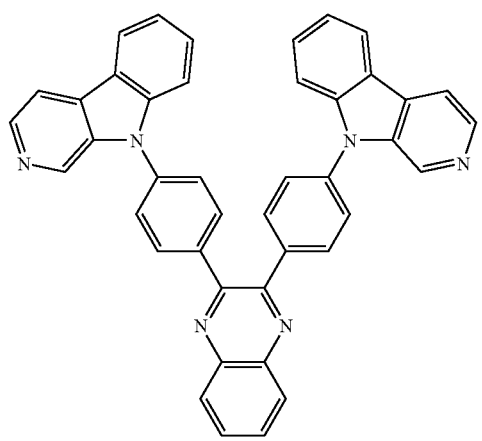
(44)
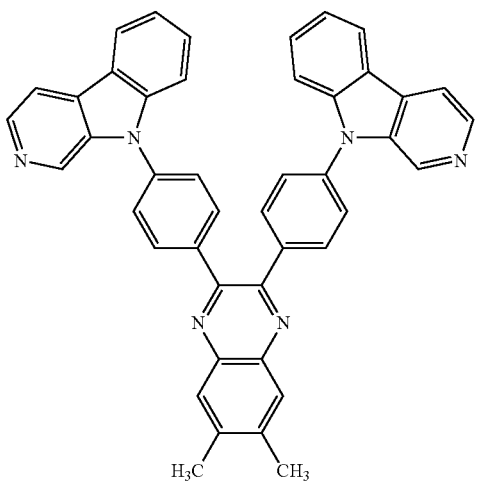
(47)
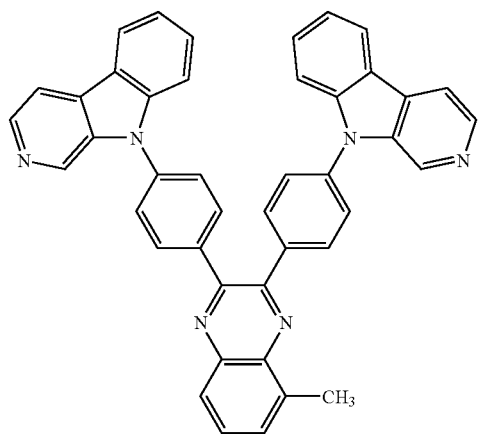
(45)
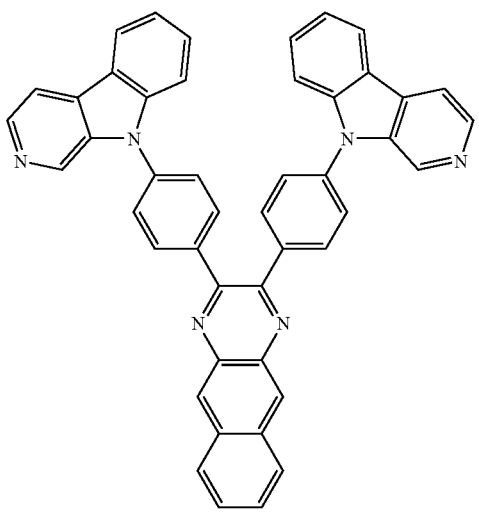
(48)

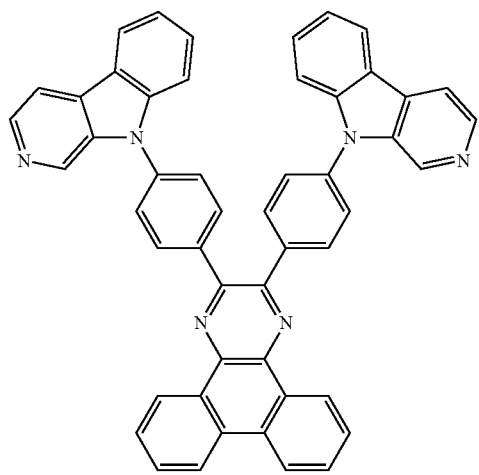
(49)
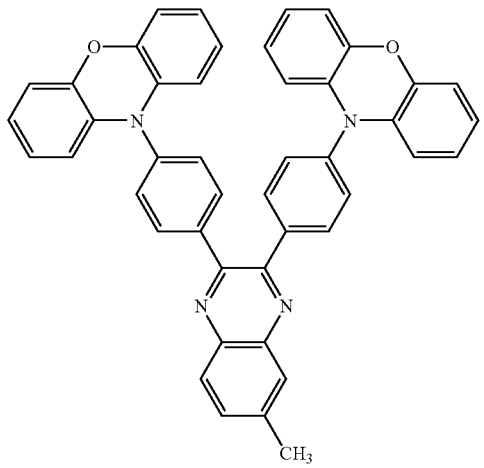
(52)
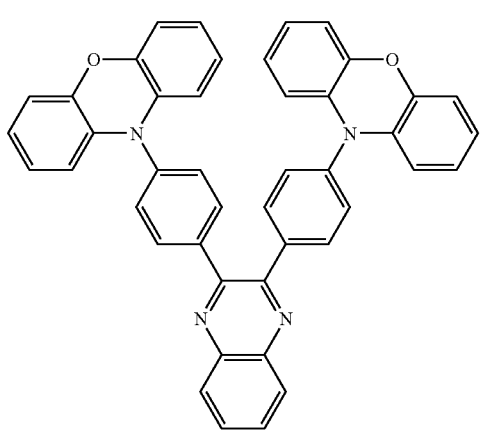
(50)
(53)
(51)
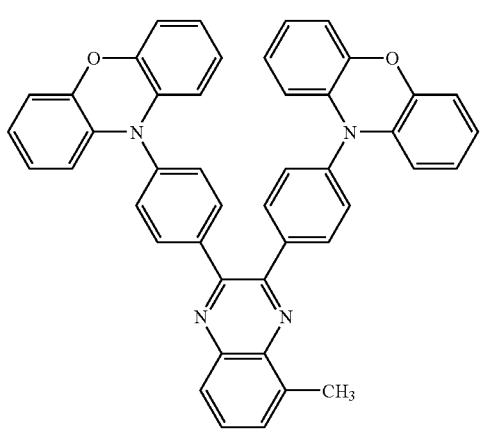
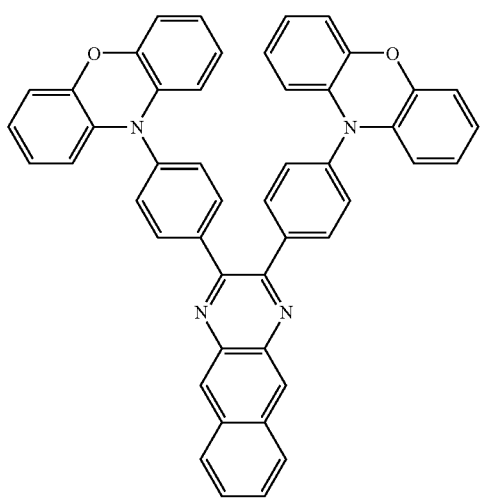
(54)

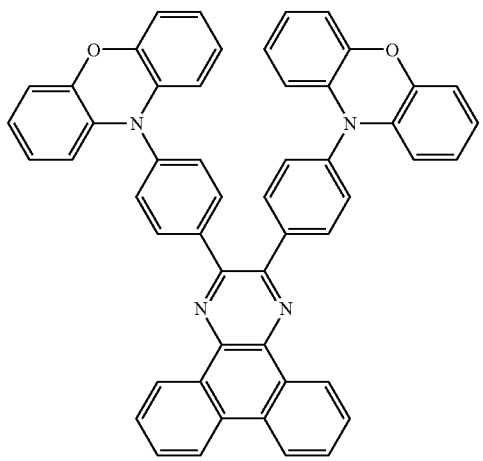
(55)
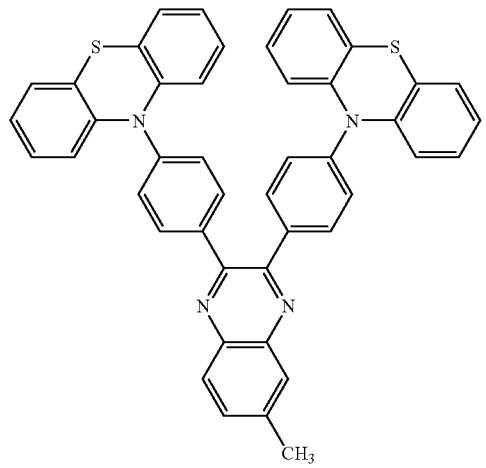
(58)
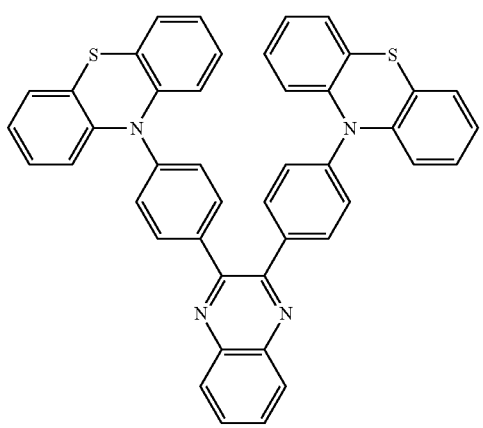
(56)
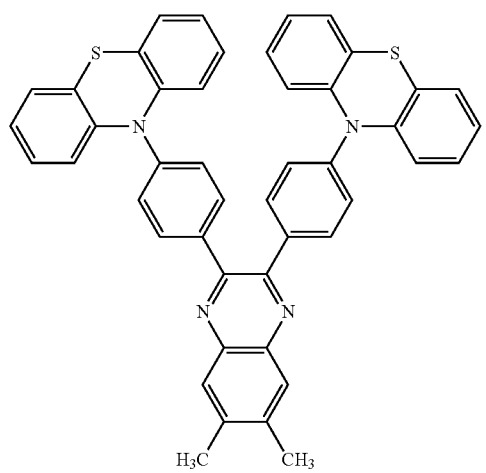
(59)
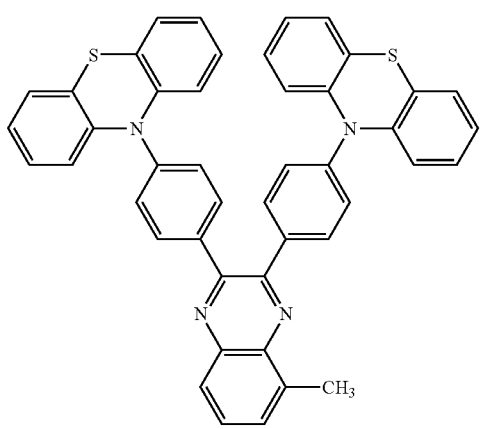
(57)
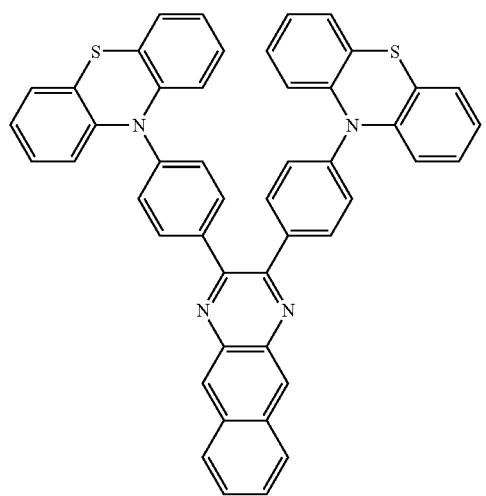
(60)

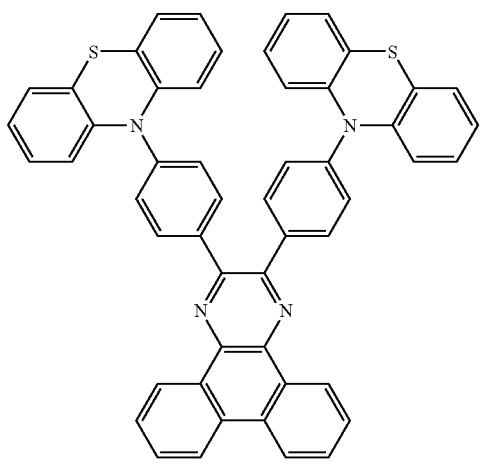
(61)
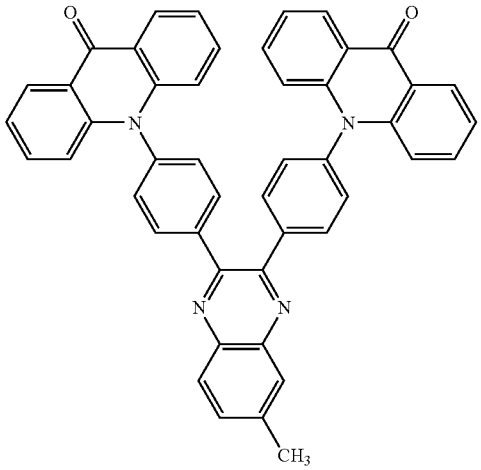
(64)
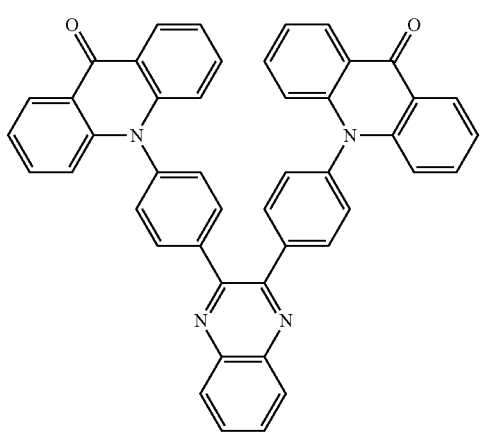
(62)
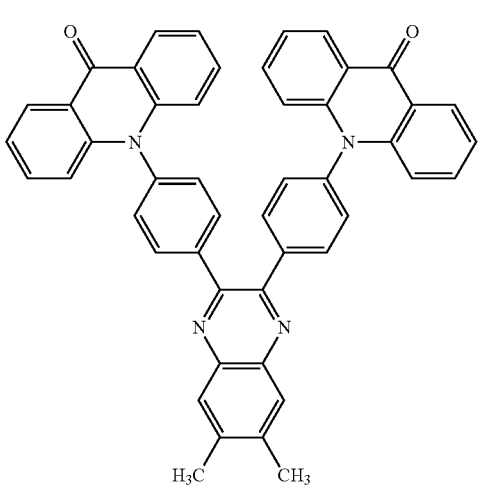
(65)
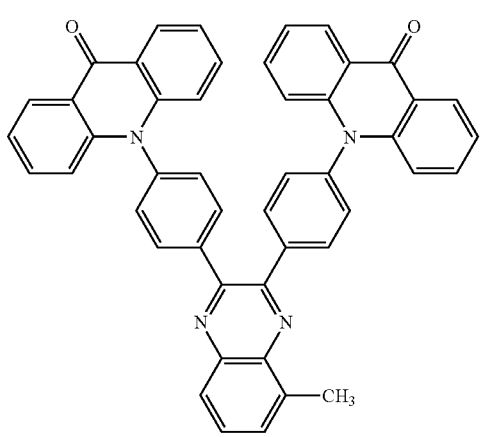
(63)
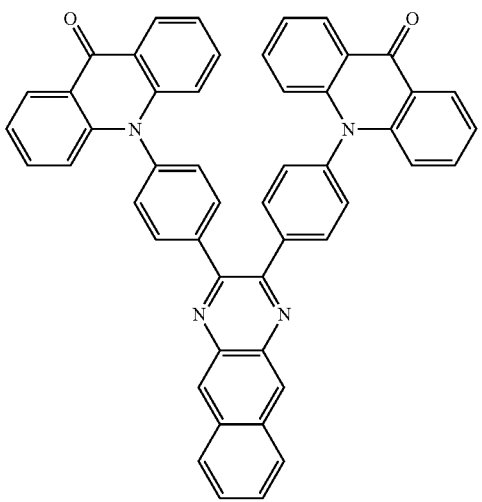
(66)

-continued (67)

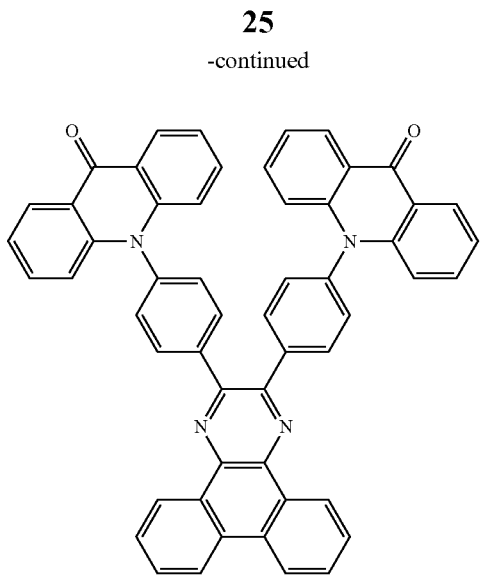

The aforementioned quinoxaline derivative of the present invention has a bipolar property and also a light emitting property. Also not easily containing a microcrystalline component at a film formation by an evaporation method, it has a satisfactory film forming property.

An example of a synthesizing method for the quinoxaline derivative of the present invention will be shown, taking the compound represented by the structural formula (10) above as an example. The quinoxaline derivative represented by the structural formula (10) above of the present invention can be obtained, for example, by a following synthesizing scheme.

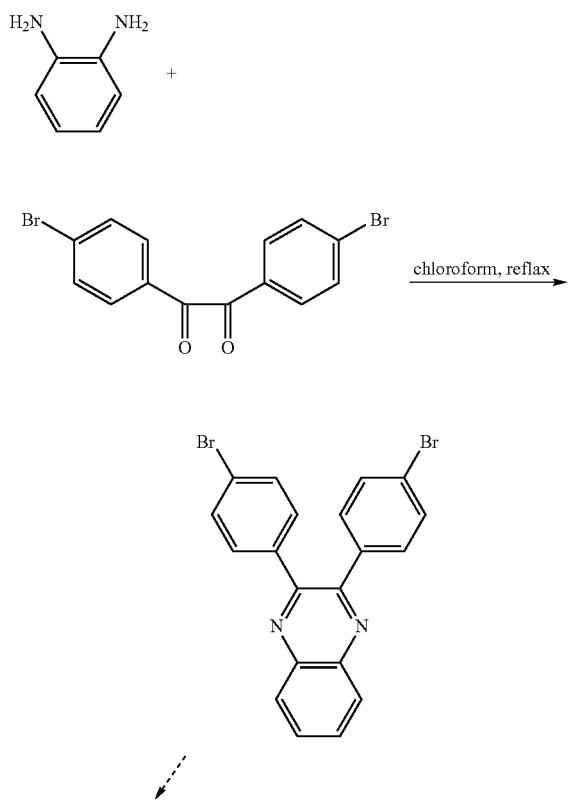

-continued

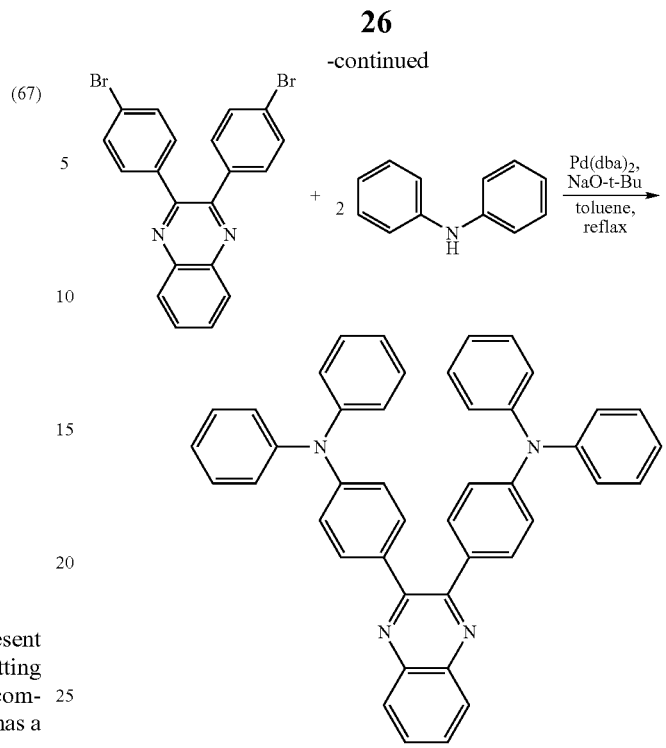

Also other compounds can be obtained, as shown above, by a method utilizing a dibromo compound of diphenylquinoxaline. However, the method for synthesizing the quinoxaline derivative of the present invention is not limited to such method.

Another structure of the present invention is an organic semiconductor device utilizing the quinoxaline derivative represented by the general formula (1), (2) or (6).

The organic semiconductor device can be, for example, an electric field light emitting device, an organic transistor, or an organic solar cell.

Another structure of the present invention is an electric field light emitting device characterized in including a quinoxaline derivative represented by the general formula (1), (2) or (6) between a pair of electrodes.

The quinoxaline derivative of the present invention, having a bipolar property and a light emitting property, can be used as a light emitting layer of an electric field light emitting device, without particularly including a dopant (guest material). Also owing to the bipolar property, the light emitting portion is not easily deviated at the interface of the laminated films, and an electric field light emitting device of a satisfactory light emitting property can be prepared with little change in the light emission spectrum and little decrease in the light emission efficiency resulting from an interaction such as an exciplex.

The quinoxaline derivative of the present invention, having a light emitting property, can be employed as a guest material (light emitting member) in the light emitting layer of the electric field light emitting device.

Also the quinoxaline derivative of the present invention, having a bipolar property and not easily containing a microcrystalline component at a film formation thereby showing a satisfactory film forming property, can be employed as a host material in the light emitting layer of the electric field light emitting device. In case of use as the host material, there can be obtained a light emission color resulting from a guest material, or a mixed light emission color of a light emission color resulting from the quinoxaline derivative of the present invention and a light emission color resulting from the guest material.

Particularly in case the quinoxaline derivative of the present invention is employed as a host material, a phosphorescent material showing a light emission from a triplet excited state is used as the guest material to obtain an electric field light emitting device of a high current efficiency and a low driving voltage. Therefore, an electric field light emitting device having the light emitting layer containing the quinoxaline derivative of the present invention and a phosphorescent material showing a light emission from a triplet excited state is also included in the present invention. In such case, the phosphorescent material preferably has a peak of a light emission spectrum from 560 to 700 nm.

EFFECT OF THE INVENTION

The present invention allows to obtain a quinoxaline derivative having a bipolar property and a light emitting property. Also the use of the quinoxaline derivative of the present invention allows to prepare an electric field light emitting device in which the light emitting portion is not easily deviated at the interface of the laminated films, and which shows a satisfactory light emitting property with little change in the light emission spectrum and little decrease in the light emission efficiency resulting from an interaction such as an exciplex. Furthermore, the use of the quinoxaline derivative of the present invention allows to prepare a satisfactory electric field light emitting device with little device defects such as a dielectric breakdown by an electric field concentration.

DETAILED DESCRIPTION OF THE PRESENTLY PREFERRED EMBODIMENTS

Embodiment Mode 1

As one aspect of the present invention, an electric field light emitting device which is an organic semiconductor device utilizing a quinoxaline derivative of the present invention will be explained with reference to FIG. 1.

Figure 1:
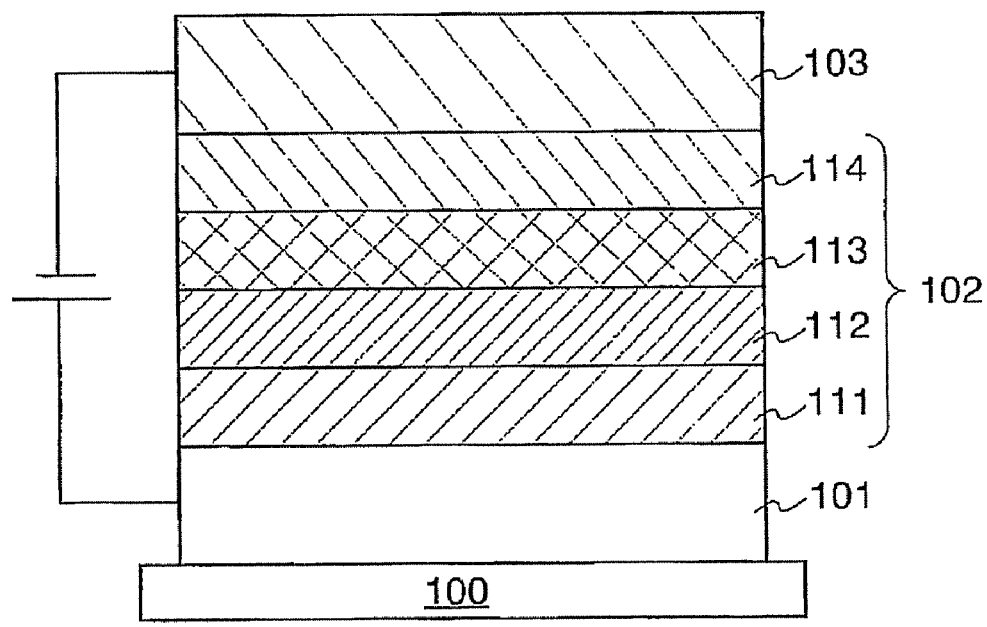
FIG. 1 is a view for explaining one aspect of an electric field light emitting device of the present invention.

In FIG. 1, there is shown a structure in which a first electrode 101 is formed on a substrate 100, an electric field light emitting layer 102 is formed on the first electrode 101, and a second electrode 103 is formed thereon.

A material to be employed for the substrate 100 can be a material employed in conventional electric field light emitting devices, and it can be constituted for example of glass, quartz, transparent plastics or the like.

In the present embodiment mode, the first electrode 101 functions as an anode, and the second electrode 103 functions as a cathode.

More specifically, the first electrode 101 is formed by an anode material, and the anode material employable in this case is preferably a metal, an alloy, an electrically conductive compound, and a mixture thereof having a large work function (work function equal to or higher than 4.0 eV). As a specific example of the anode material, there can be used indium tin oxide (ITO), or indium zinc oxide (IZO) formed by mixing indium oxide with zinc oxide (ZnO) of 2-20%, or also gold (Au), platinum (Pt), nickel (Ni), tungsten (W), chromium (Cr), molybdenum (Mo), iron (Fe), cobalt (Co), copper (Cu), palladium (Pd) or a nitride of a metal material (TiN).

On the other hand, as the cathode material to be used for forming the second electrode 103 there is preferably employed a metal, an alloy, an electrically conductive compound, and a mixture thereof having a small work function (work function equal to or lower than 3.8 eV). Specific examples of the cathode material include an element of the group 1 or 2 of the periodic table, namely an alkali metal such as lithium (Li) or cesium (Cs), an alkali earth metal such as magnesium (Mg), calcium (Ca) or strontium (Sr), and an alloy including these (Mg:Ag, Al:Li). However, by forming a layer of a function promoting an electron injection between the second electrode 103 and the light emitting layer and in lamination with such second electrode, it is possible to use various conductive material such as Al, Ag, ITO as the second electrode 103 regardless of the magnitude of the work function.

For the layer of the function promoting the electron injection, a compound of an alkali metal or an alkali earth metal, such as lithium fluoride (LiF), cesium fluoride (CsF) or calcium fluoride (CaF$_2$), can be used. In addition, it is also possible to use a material having an electron transporting property, in which an alkali metal or an alkali earth metal is contained, for example Alq containing magnesium (Mg).

The anode material and the cathode material mentioned above are formed as thin films by an evaporation method or a sputtering method, thereby respectively forming the first electrode 101 and the second electrode 103.

The electric field light emitting device of the present invention has a structure in which a light generated by a recombination of carriers in the electric field light emitting layer 102 is emitted to the exterior from either of the first electrode 101 and the second electrode 102, or both thereof. Thus, in case the light is emitted from the first electrode 101, the first electrode 101 is formed with a light transmitting material, and, in case the light is emitted from the side of the second electrode 103, the second electrode 103 is formed with a light transmitting material.

The electric field light emitting layer 102 is formed by laminating plural layers, and, in the present embodiment mode, it is formed by laminating a hole injecting layer 111, a hole transporting layer 112, a light emitting layer 113 and an electron transporting layer 114.

As a hole injecting material for forming the hole injecting layer 111, a compound of phthalocyanine type is effective. For example, phthalocyanine (abbreviation: $H_2Pc$), copper phthalocyanine (abbreviation: CuPc) etc., can be employed.

As a hole transporting material for forming the hole transporting layer 112, a compound of aromatic amine type (namely having a benzene ring-nitrogen bond) is suitable. Widely employed materials include, for example, 4,4'-bis[N-(3-methylphenyl)-N-phenyl-amino]-biphenyl (abbreviation: TPD), or its derivatives such as 4,4'-bis[N-(1-naphthyl)-N-phenyl-amino]-biphenyl (abbreviation: α-NPD), or star burst aromatic amine compounds, such as 4,4',4"-tris(N,N-diphenyl-amino)-triphenylamine (abbreviation: TDATA), or 4,4', 4"-tris[N-(3-methylphenyl)-N-phenyl-amino]-triphenylamine (abbreviation: MTDATA).

The light emitting layer 113 is formed by the quinoxaline derivative of the present invention represented by the general formula (1), (2) or (6). The quinoxaline derivative of the present invention, having a bipolar property and a light emitting property, can be employed as the light emitting layer without a particular doping with a guest material having a light emitting property.

The quinoxaline derivative of the present invention is considered to have a bipolar character, as an arylamine skeleton of an electron donating property is introduced into a quinoxaline skeleton having an electron transporting property.

As an electron transporting material in case of forming the electron transporting layer 114, a metal complex having a quinoline skeleton or a benzoquinoline skeleton is preferable, such as tris(8-quinolinolato)aluminum (abbreviation: $Alq_3$), tris(5-methyl-8-quinolinolato)aluminum (abbreviation: $Almq_3$), bis(10-hydroxybenzo[h]-quinolinato)beryllium (abbreviation: $BeBq_2$), or BAlq mentioned above. There is also available a metal complex having an oxazole or thiazole ligand, such as bis[2-(2-hydroxyphenyl)-benzoxazolato]zinc (abbreviation: $Zn(BOX)_2$) or bis[2-(2-hydroxyphenyl-benzothiazolato)zinc (abbreviation: $Zn(BTZ)_2$). In addition to the metal complex, 2-(4-biphenyl)-5-(4-tert-butylphenyl)-1, 3,4-oxadiazole (abbreviation: PBD), 1,3-bis[5-(p-tert-butylphenyl)-1,3,4-oxadiazol-2-yl]benzene (abbreviation: OXD-7), 3-(4-tert-butylphenyl)-4-phenyl-5-(4-biphenylyl)-1,2,4-triazole (abbreviation: TAZ), 3-(4-tert-butylphenyl)-4-(4-ethylphenyl)-5-(4-biphenyl-1)-1,2,4-triazole (abbreviation: p-EtTAZ), basophenanthroline (abbreviation: BPhen), basocuproin (abbreviation: BCP), and the like can be used as the electron transporting material.

Based on the foregoing, an electric field light emitting device can be prepared with the light emitting layer 113 formed by the quinoxaline derivative of the present invention, the hole injecting layer 111, the hole transporting layer 112, and the electron transporting layer 114 formed by a low molecular material. The hole injecting layer 111, the hole transporting layer 112, and the electron transporting layer 114 are not limited to a low molecular material, but can also be formed by a high molecular material.

Figure 2:
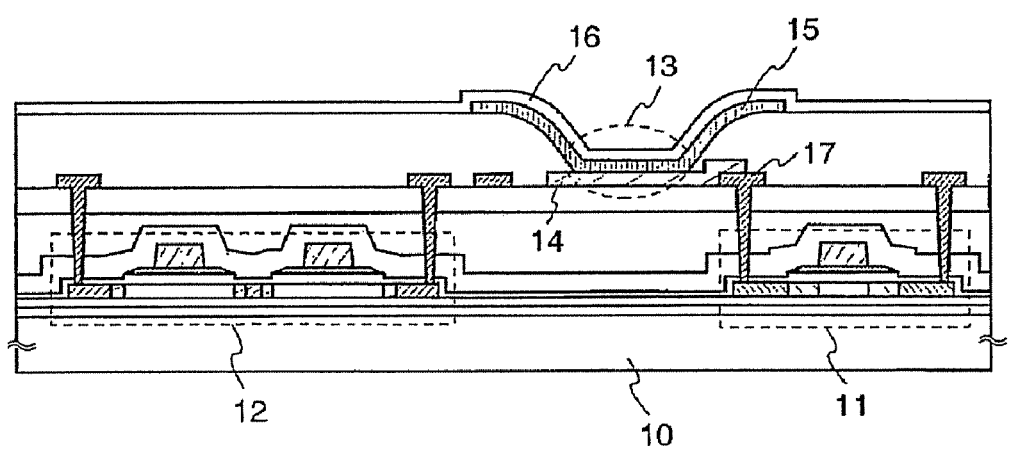
FIG. 2 is a view for explaining one aspect of an electric field light emitting device of the present invention.

In the present embodiment mode, the electric field light emitting device is formed on the substrate 100, but the electric field light emitting device may also be formed, as shown in FIG. 2, on a thin film transistor (TFT), with an electrical connection to the TFT. In FIG. 2, 10 indicates a substrate, broken-lined areas 11, 12 indicate TFT, 14 indicates a first electrode, 15 indicates a layer containing a light emitting substance, 16 indicates a second electrode, and 17 indicates a wiring, wherein a laminated portion of the first electrode 14, the layer 15 containing the light emitting substance and the second electrode 16 functions as a light emitting device 13. Thus there can be prepared a light emitting apparatus of active matrix type in which the drive of the light emitting device is controlled by the TFT. The structure of the TFT is not particularly restricted and can be a top gate type or a bottom gate type.

The electric field light emitting layer, in addition to the structure shown in the present embodiment mode, may also have a laminated structure such as hole injecting layer\light emitting layer\electron injecting layer. Also since the quinoxaline derivative of the present invention has a hole transporting property and an electron transporting property, and also a light emitting property, the electric field light emitting layer may have a structure utilizing the quinoxaline derivative of the present invention in a single layer.

The quinoxaline derivative of the present invention, being a material having a bipolar property and a light emitting property, can be employed, as indicated in the present embodiment mode, as a light emitting layer without including a dopant (guest material) or the like. Also owing to the bipolar property, the light emitting portion is not easily deviated at the interface of the laminated films, and an electric field light emitting device of a satisfactory light emitting property can be prepared with little change in the light emission spectrum and little decrease in the light emission efficiency resulting from an interaction such as an exciplex. Also as the contained microcrystalline component is very few in the film formation to provide a satisfactory film forming property, there can be prepared a satisfactory electric field light emitting device with low device defects such as a dielectric breakdown by an electric field concentration. Also the quinoxaline derivative of the present invention, being a material having a carrier transporting property (electron transporting property and hole transporting property), can reduce, by the use in the light emitting layer, a drive voltage of the electric field light emitting device.

Embodiment Mode 2

This embodiment mode explains an electric field light emitting device employing the quinoxaline derivative of the present invention as a guest material.

The quinoxaline derivative of the present invention, having a light emitting property, can also be used as a guest material (light emitter) for obtaining a light emission of blue to blue-green color.

The quinoxaline derivative of the present invention, being a material having a carrier transporting property, can reduce, by the use as a guest material, a drive voltage of the electric field light emitting device.

In such case, there can be adopted a device structure having an electric field light emitting layer (a structure of single layer or laminated layers) employing, as a light emitting layer, an organic compound layer containing the quinoxaline derivative represented by the general formula (1), (2) or (6), sandwiched between a pair of electrodes (an anode and a cathode). For example, in an electric field light emitting device having a device structure of anode\hole injecting layer\hole transporting layer\light emitting layer\electron transporting layer\cathode, anode\hole injecting layer\light emitting layer\electron transporting layer\cathode, anode\hole injecting layer\hole transporting layer\light emitting layer\electron transporting layer\electron injecting layer\cathode, anode\hole injecting layer\hole transporting layer\light emitting layer\hole blocking layer\electron transporting layer\cathode, or anode\hole injecting layer\hole transporting layer\light emitting layer\hole blocking layer\electron transporting layer\electron injecting layer\cathode, a light emitting layer containing the quinoxaline derivative represented by the general formula (1), (2) or (6) as a guest material can be used.

As the host material, a known material can be employed such as, in addition to the hole transporting material and the electron transporting material described in the embodiment mode 1, 4,4'-bis(N-carbazolyl)-biphenyl (abbreviation: CBP), 2,2',2''-(1,3,5-benzenetri-yl)-tris[1-phenyl-1H-benzimidazole] (abbreviation: TPBI), or 9,10-di(2-naphthyl)anthracene (abbreviation: DNA).

In particular, a quinoxaline derivative represented by the foregoing structural formula (10) as a guest material and DNA as a host material allow to obtain a high light emitting efficiency and a light emission of highly pure blue color.

The electric field light emitting device of the present embodiment mode can be prepared, as shown in the embodiment mode 1, on a substrate or can be prepared on a TFT as an electric field light emitting device electrically connected with the TFT.

Embodiment Mode 3

The present embodiment mode explains an electric field light emitting device employing the quinoxaline derivative of the present invention as a host material.

The quinoxaline derivative of the present invention, having a bipolar property and showing very few microcrystalline component contained in a film formation thereby providing a satisfactory film forming property, can be used as a host material.

Also the quinoxaline derivative of the present invention, being a material having a carrier transporting property as explained in the foregoing, can reduce, when employed as a host material, a drive voltage of the electric field light emitting element.

In case of use as a host material, there can be obtained a light emission color resulting from a guest material, or a mixed light emission color of a light emission color resulting from the quinoxaline derivative of the present invention and a light emission color resulting from the guest material doped in such quinoxaline derivative.

In such case, there can be adopted a device structure having an electric field light emitting layer (a structure of single layer or laminated layers) employing, as a light emitting layer, an organic compound layer containing the quinoxaline derivative represented by the general formula (1), (2) or (6), sandwiched between a pair of electrodes (anode and cathode). For example, in an electric field light emitting device having a device structure of anode\hole injecting layer\hole transporting layer\light emitting layer\electron transporting layer\cathode, anode\hole injecting layer\light emitting layer\electron transporting layer\cathode, anode\hole injecting layer\hole transporting layer\light emitting layer\electron transporting layer\electron injecting layer\cathode, anode\hole injecting layer\hole transporting layer\light emitting layer\hole blocking layer\electron transporting layer\cathode, or anode\hole injecting layer\hole transporting layer\light emitting layer\hole blocking layer\electron transporting layer\electron injecting layer\cathode, a light emitting layer containing the quinoxaline derivative represented by the general formula (1), (2) or (6) as a host material can be used.

As the guest material, a known material can be used, for example a fluorescent material such as 4-(dicyanomethylene)-2-methyl-6-(p-dimethylaminostyryl)-4H-pyran (abbreviation: DCM1), 4-(dicyanomethylene)-2-methyl-6-(julolidin-4-yl-vinyl)-4H-pyran (abbreviation: DCM2), N,N-dimethylquinacridone (abbreviation: DMQd), 9,10-diphenylanthracene (abbreviation: DPA), 5,12-diphenyltetracene (abbreviation: DPT), coumarin 6, perylene or rubrene, or a phosphorescent material such as bis(2-(2'-benzothienyl)pyridinato-N,$C^{3'}$)(acetylacetonato) iridium (abbreviation: Ir(btp)$_2$(acac)) or the like.

An electric field light emitting device for obtaining a light emission from a triple excited state by adding a phosphorescent material such as the aforementioned iridium complex is already known as a device capable of attaining a high efficiency, but a high drive voltage has been a drawback. However, the quinoxaline derivative of the present invention employed as the host allows to reduce the drive voltage.

Also the quinoxaline derivatives of the present invention relatively frequently show the light emission in a range of blue to green-yellow color. Therefore, in case of adding a phosphorescent material to the quinoxaline derivative of the present invention as a host, the phosphorescent material preferably has a light emitting wavelength at a longer wavelength than in the quinoxaline derivative, particularly in a range of yellow to red color such as about 560 to 700 nm. However such condition is not restrictive as the light emission wavelength of the quinoxaline derivative can be changed by a substituent effect.

The electric field light emitting device of the present embodiment mode can be prepared, as shown in the embodiment mode 1, on a substrate or can be prepared on a TFT as an electric field light emitting device electrically connected with the TFT.

Embodiment Mode 4

The present embodiment mode 4 illustrates a mode in which the quinoxaline derivative of the present invention is used as an active layer of a vertical type transistor (SIT) which is one of organic semiconductor derives.

Figure 16:
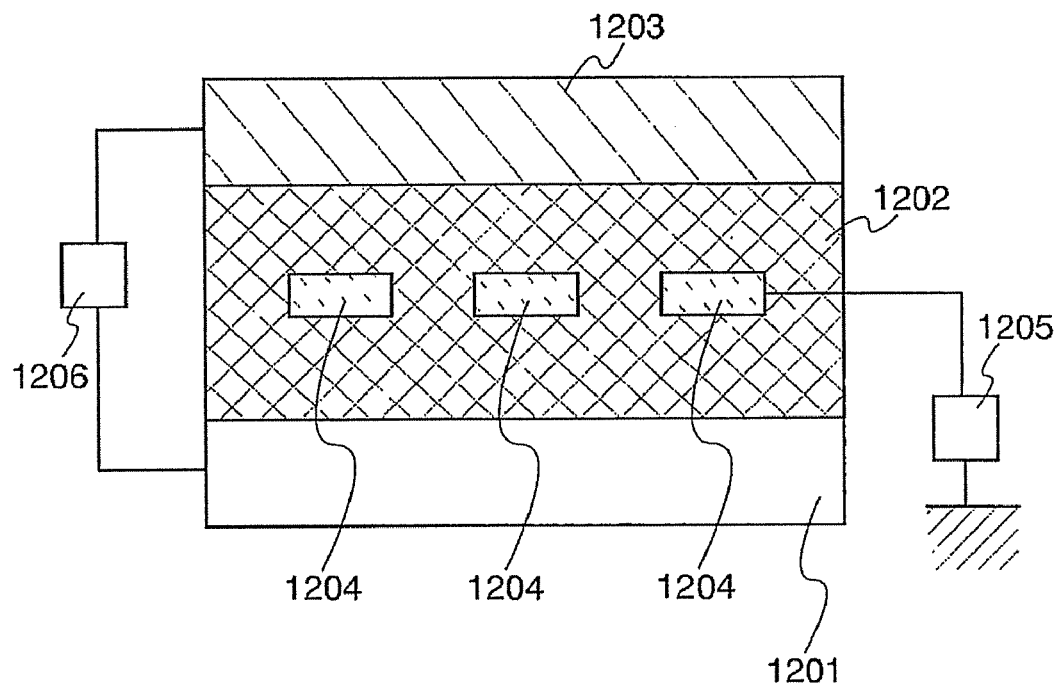
FIG. 16 is a view for explaining an organic semiconductor device in which the present invention is applied.

The device has a structure in which, as shown in FIG. 16, an active layer 1202 of a thin film shape formed by the quinoxaline derivative of the present invention is sandwiched between a source electrode 1201 and a drain electrode 1203, and a gate electrode 1204 is embedded in the active layer 1202. 1205 indicates means for applying a gate voltage, and 1206 indicates means for controlling a voltage between the source and the drain.

In such device structure, when a voltage is applied between the source and the drain in a state in which a gate voltage is not applied, a current flows as in the electric field light emitting device (on-state). When a gate voltage is applied in such state, a depletion layer is generated in the vicinity of the gate electrode 1204, whereby the current no longer flows (off-state). A function as a transistor is obtained through the above-described mechanisms.

In a vertical type transistor, as in the electric field light emitting device, a material having a carrier transporting property and a satisfactory film forming property is required for the active layer, and the quinoxaline derivative of the present invention sufficiently meets these conditions and is therefore useful.

Embodiment Mode 5

As the light emitting device of the present invention functions at a low drive voltage, a light emitting apparatus employing the present invention can be operated with a low electric power consumption. Also an electronic device utilizing such light emitting apparatus employing the present invention can be operated with a low electric power consumption.

Figure 17:
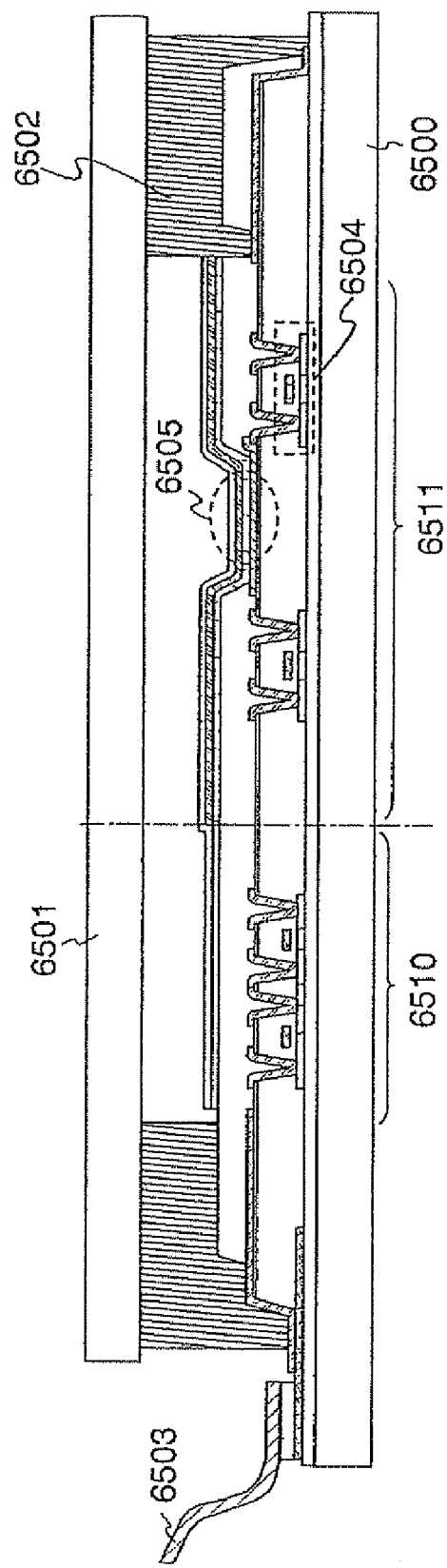
FIG. 17 is a cross-sectional view for explaining a light emitting apparatus in which the present invention is applied.
Figure 18:
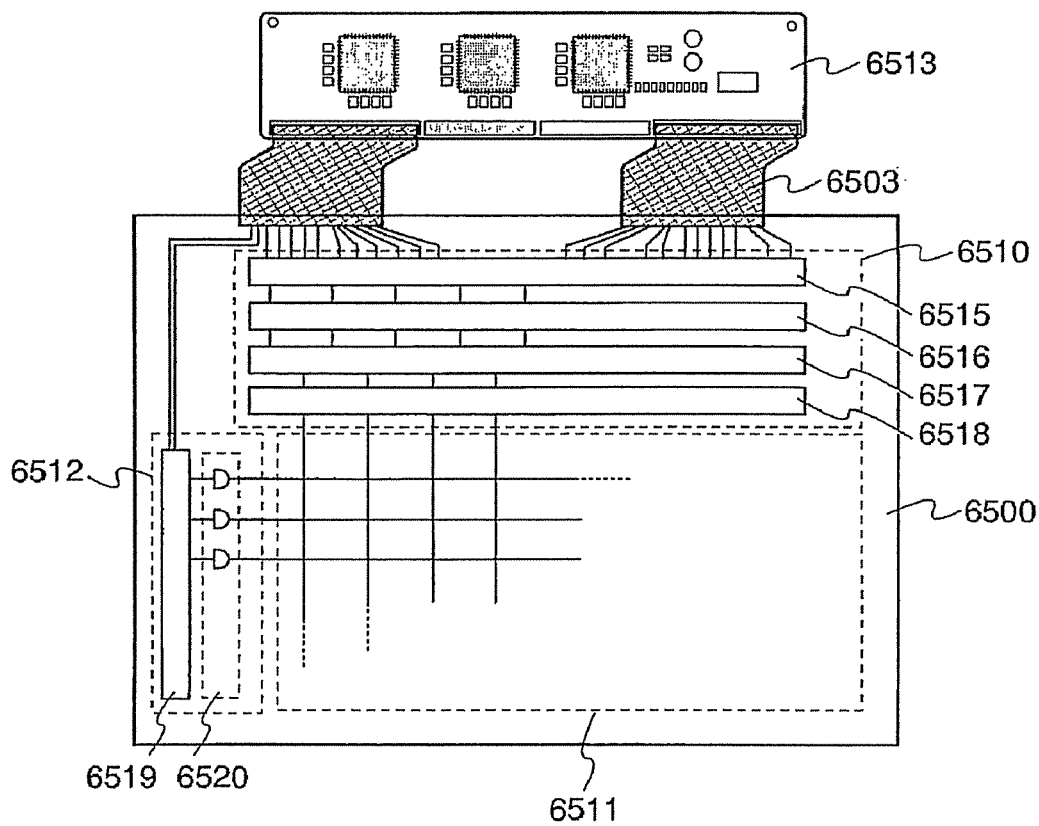
FIG. 18 is a plan view for explaining a light emitting apparatus in which the present invention is applied.

Thus, the present embodiment mode explains a light emitting apparatus and an electronic device employing the present invention, with reference to FIGS. 17-19.

A light emitting apparatus formed by providing a plurality of the light emitting device of the present invention on a substrate can be installed, after mounting an external input terminal and sealing, as a display apparatus in various electronic devices.

The present embodiment mode explains a light emitting apparatus after sealing and an electronic device mounted with such light emitting apparatus, with reference to FIGS. 17-19. However, FIGS. 17-19 merely show an embodiment mode, and the structure of the light emitting apparatus is not limited to such structure.

FIG. 17 is a cross-sectional view of a light-emitting apparatus after sealing. A substrate 6500 and a sealing substrate 6501 are adhered with a sealing agent 6502 so as to enclose a transistor 6504 and a light-emitting device 6505. At an end portion of the substrate 6500, an FPC (flexible printed circuit) 6503 constituting an external input terminal is mounted. An internal region enclosed by the substrate 6500 and the sealing substrate 6501 is filled with an inert gas such as nitrogen or a resinous material.

FIG. 18 is a schematic view, seen from above, of a light emitting apparatus in which the present invention is applied. Referring to FIG. 18, a broken-lined area 6510 indicates a drive circuit portion (source side drive circuit), 6511 indicates a pixel portion, and 6512 indicates a drive circuit portion (gate side drive circuit). In the pixel portion 6511, light emitting devices of the present invention are provided. The drive circuit portions 6510 and 6512 are connected by the FPC 6503 constituting the external input terminal and a group of wirings formed on the substrate 6500. By receiving a video signal, a clock signal, a start signal, a reset signal etc. from the FPC (flexible printed circuit) 6503, signals are entered into the source side drive circuit 6510 and the gate side drive circuit 6512. A printed wiring board (PWB) 6513 is mounted on the FPC 6503. The drive circuit portion 6510 includes a shift register 6515, a switch 6516, and memories (latches) 6517, 6518, while the drive circuit portion 6512 includes a shift register 6519 and a buffer 6520. Also other functions may further be provided. Also the drive circuit portion need not be provided on the same substrate as that for the pixel portion 6511, and it may be provided outside the substrate, for example utilizing a TCP in which an IC chip is mounted on an FPC in which a wiring pattern is formed.

FIG. 19 shows an embodiment of an electronic device in which a light emitting apparatus embodying the present invention is mounted.

Figure 19A:
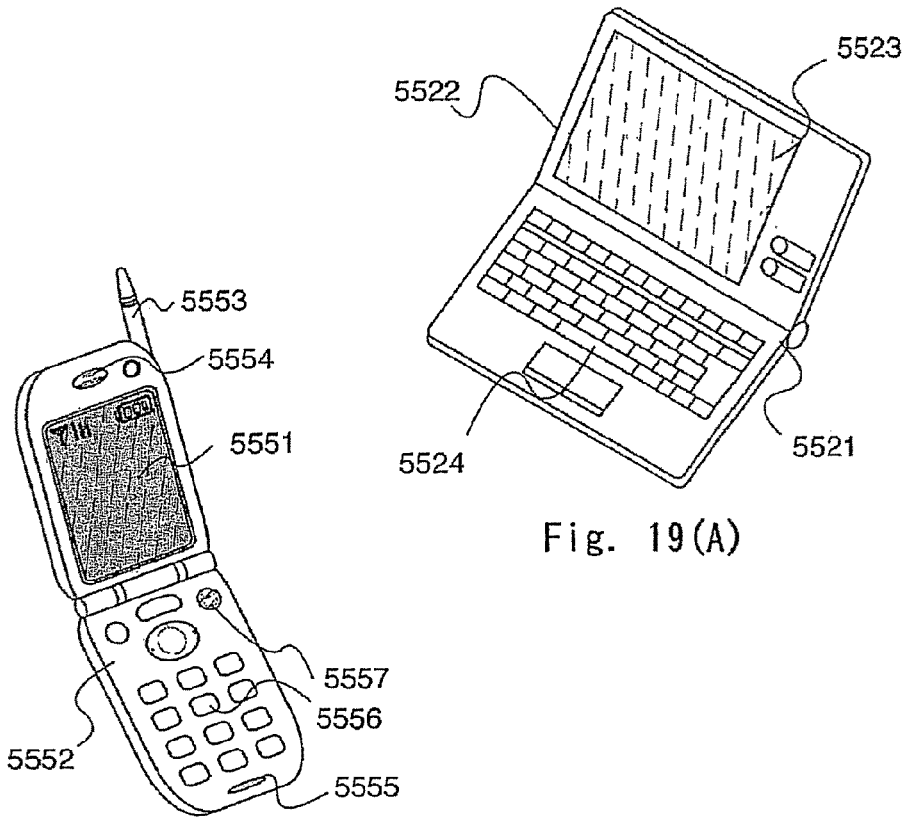
FIGS. 19(a)-19(c) are views for explaining an electronic device in which the present invention is applied.

FIG. 19(A) is a notebook type personal computer prepared applying the present invention, and is constituted by a main body 5521, a casing 5522, a display portion 5523, a keyboard 5524 etc. The personal computer can be completed by incorporating, as a display portion, a light emitting apparatus having the light emitting device of the present invention.

Figure 19B:

FIG. 19(B) is a portable telephone prepared applying the present invention, and a main body 5552 is constituted by a display portion 5551, an audio output portion 5554, an audio input portion 5555, operation switches 5556, 5557, an antenna 5553 etc. The portable telephone can be completed by incorporating, as a display portion, a light emitting apparatus having the light emitting device of the present invention.

Figure 19C:
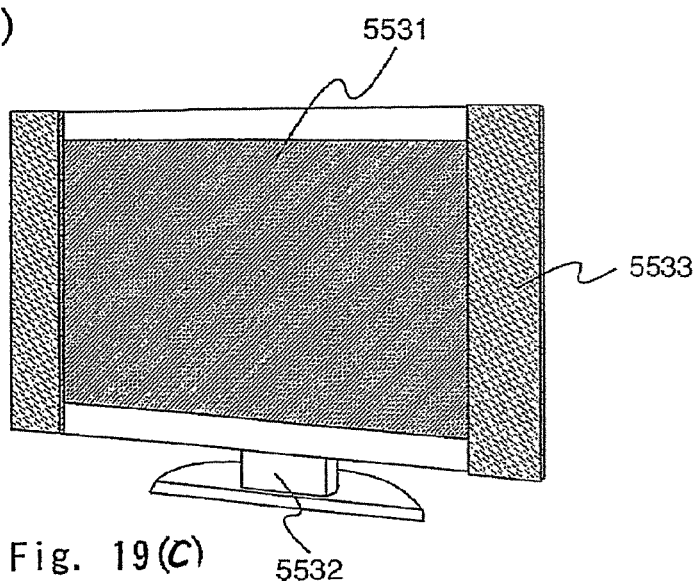

FIG. 19(C) is a television receiver prepared applying the present invention, and is constituted of a display portion 5531, a casing 5532, a speaker 5533 etc. The television receiver can be completed by incorporating, as a display portion, a light emitting apparatus having the light emitting device of the present invention.

As explained above, the light emitting apparatus of the present invention is suitable for use as a display portion of various electronic devices.

The present embodiment describes a notebook type personal computer, but the light emitting apparatus having the light emitting device of the present invention may also be mounted in a car navigation or an illuminating apparatus.

EMBODIMENTS

Embodiment 1

Synthesis Example 1

This synthesis example 1 specifically shows a synthesis example of the quinoxaline derivative of the present invention represented by the foregoing structural formula (10) (hereinafter represented as TPAQn).

Synthesis of 2,3-bis(4-bromophenyl)quinoxaline

At first 10 g (27.4 mmol) of 4-bromobenzyl and 3.5 g (33.5 mmol) of o-phenylenediamine were charged in a 500 ml-eggplant-shaped flask, and agitated and refluxed in chloroform for 8 hours.

Then, after cooling to the room temperature, remaining o-phenylenediamine was eliminated by column chromatography whereby 2,3-bis(4-bromophenyl)quinoxaline was obtained.

Synthesis of TPAQn

Then, 4.40 g (10.0 mmol) of thus obtained 2,3-bis(4-bromophenyl)quinoxaline were weighed and charged in a three-necked flask, and dissolved in 75 ml of toluene under a nitrogen flow. Then, 0.22 g (0.2 mmol) of $Pd(dba)_2$, 2.88 g (30 mmol) of NaO-t-Bu and 3.46 g (20.4 mmol) of diphenylamine were added, also 1.8 ml of a 10 wt. % hexane solution of tri(t-butylphosphin) and agitation under heat was executed for 8 hours at 80° C.

Figure 3:
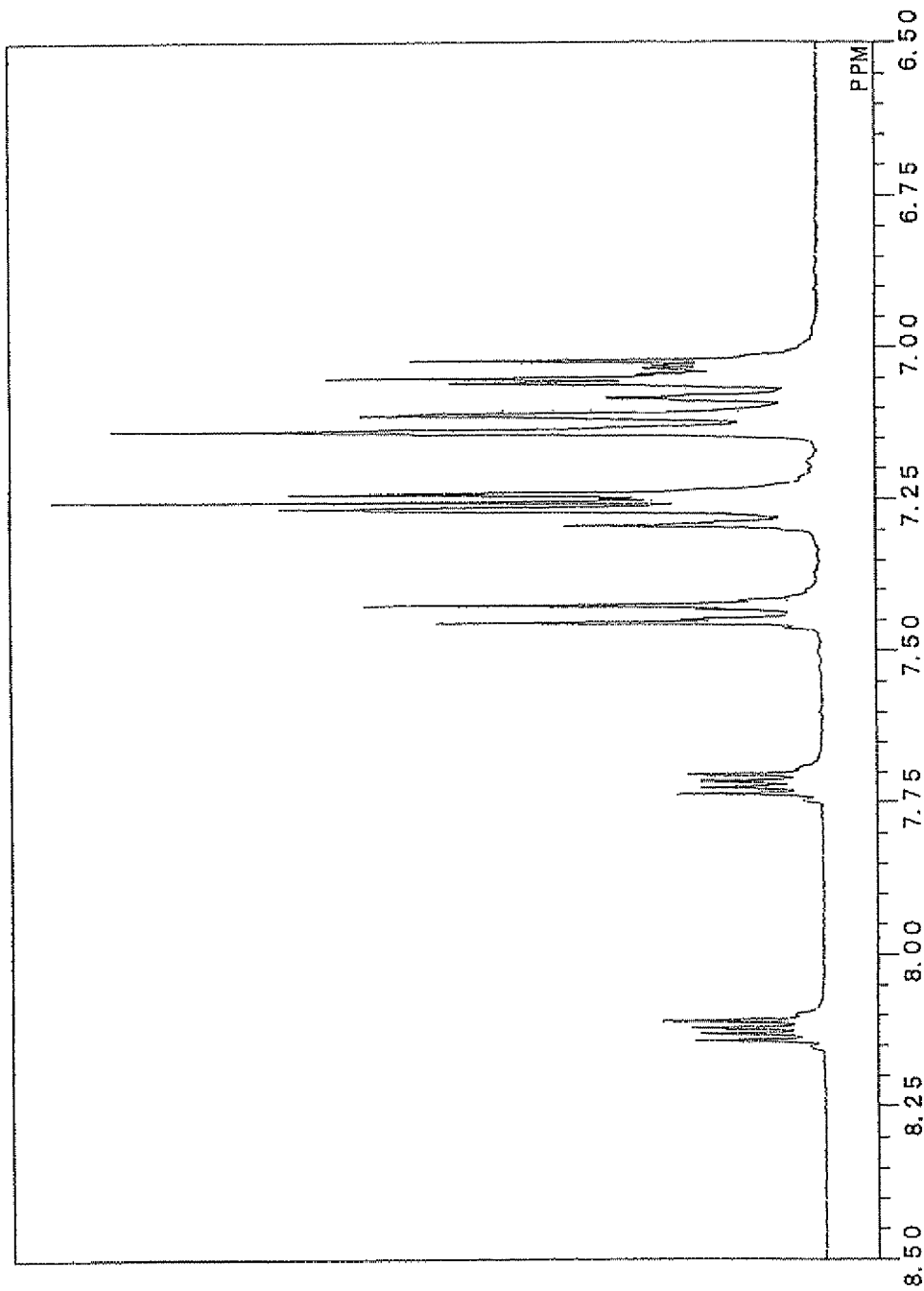
FIG. 3 is a $^1$H-NMR chart of TPAQn.

Then, after cooling to the room temperature, the reaction is terminated by adding water, and an extraction was made with chloroform. Then, after washing with saturated salt solution, a drying was executed with $MgSO_4$. Thereafter, a recrystallization was executed from chloroform to obtain desired TPAQn (yellow-green crystal, yield 2.7 g (yield: 44%)). FIG. 3 shows a $^1$H-NMR chart of TPAQn. The obtained TPAQn had a decomposition temperature of 411° C. and was easily capable of film formation by a vacuum evaporation method by a resistance heating. A uniform film was formed without crystallization, coagulation or the like. In a measurement with a differential scanning calorimeter (Pyris 1DSC, manufactured by Perkin Elmer Inc.), a glass transition point was observed at 93° C. and a melting point was observed in two positions at 214 and 220° C.

Figure 4A:
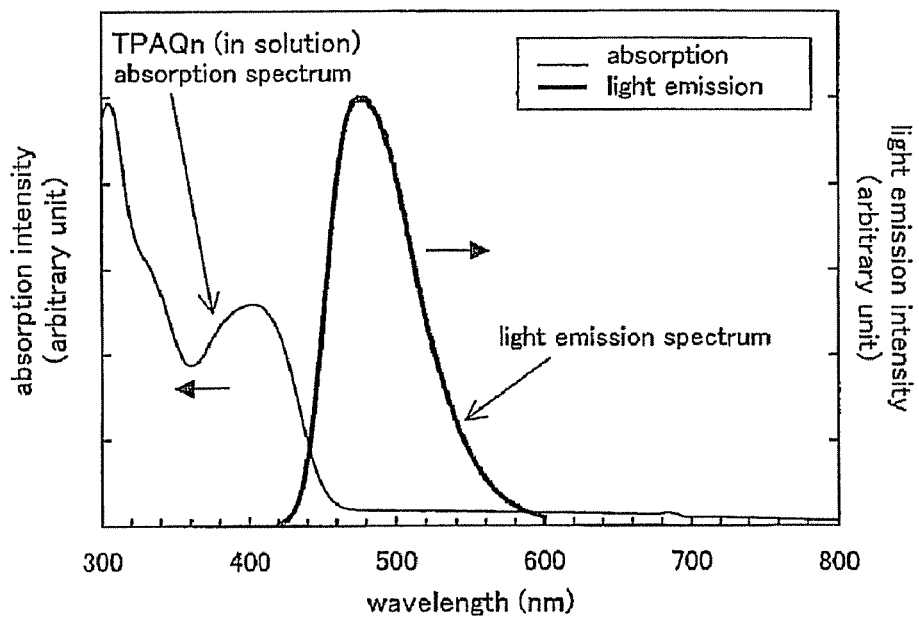
FIGS. 4(a)-4(b) are views showing an absorption-light emission spectrum of TPAQn.
Figure 4B:
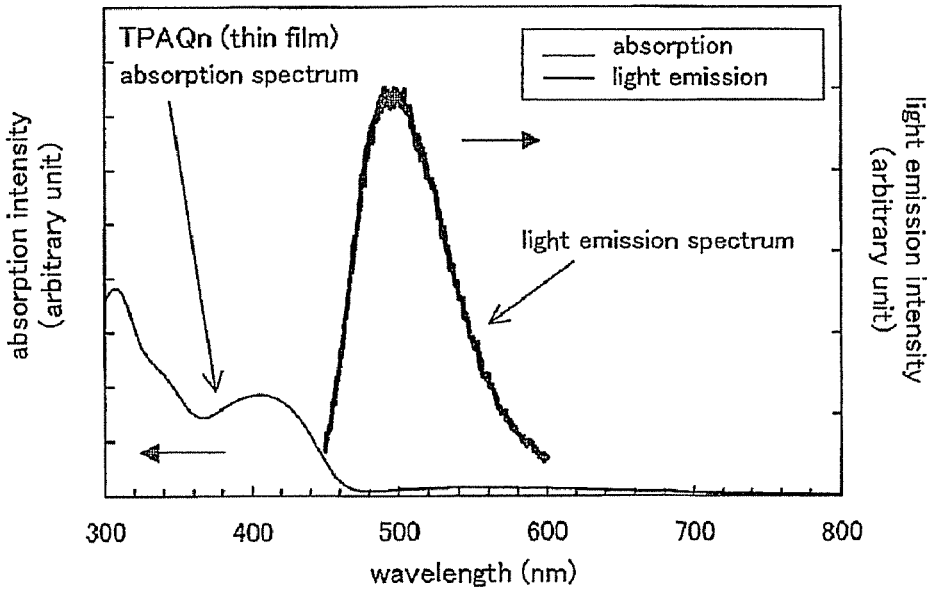

An absorption-light emission spectrum of TPAQn in a toluene solution is shown in FIG. 4(a), and an absorption-light emission spectrum of a thin film is shown in FIG. 4(b). In the toluene solution, a blue light emission having a peak at 480 nm was obtained, and, in the thin film state, a blue-green light emission having a peak at 500 nm was obtained. Also a HOMO level in a thin film state, measured by a photoelectron spectroscopy (AC-2, manufactured by Riken Keiki Co.) in the air, was −5.46 eV. Also, taking an absorption end of the absorption spectrum shown in FIG. 4(b) as an energy gap, a LUMO level was −2.76 eV.

Also when a carrier mobility of the evaporated film of TPAQn was measured by a time of flight (TOF) method, a hole mobility was in the order of $10^{-6}$ cm$^2$/Vs, and an electron mobility was in the order of $10^{-5}$ cm$^2$/Vs. Based on these facts, it was identified that TPAQn was excellent in the transporting property for both hole and electron carriers, and also had a bipolar property.

Synthesis Example 2

A quinoxaline derivative of the present invention represented by the foregoing structural formula (38) (hereinafter represented as CzQn) can be obtained by employing carbazole instead of diphenylamine in the synthesis example 1.

The obtained CzQn had a decomposition temperature of 447° C. and was easily capable of film formation by a vacuum evaporation method by a resistance heating. A uniform film was formed without crystallization, coagulation or the like.

Figure 5A:
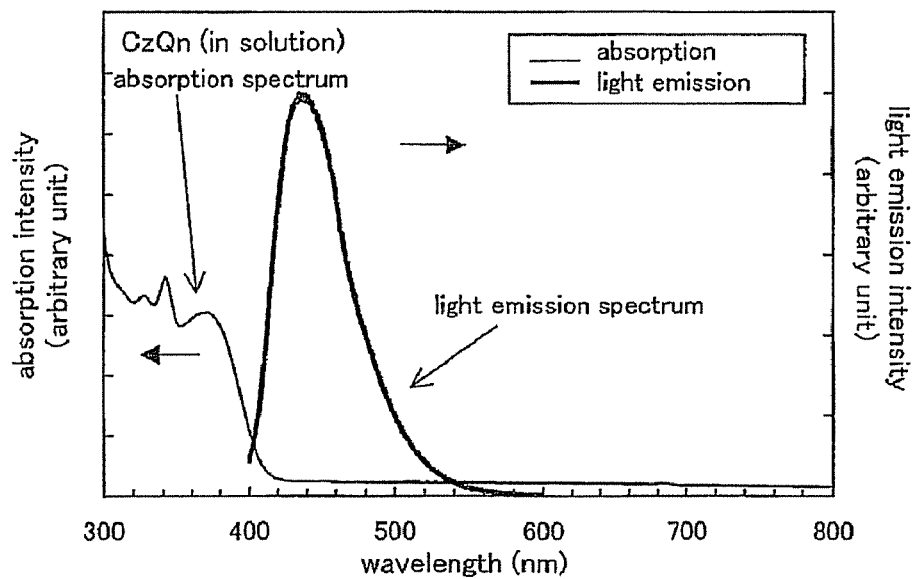
FIGS. 5(a)-5(b) are views showing an absorption-light emission spectrum of CzQn.
Figure 5B:
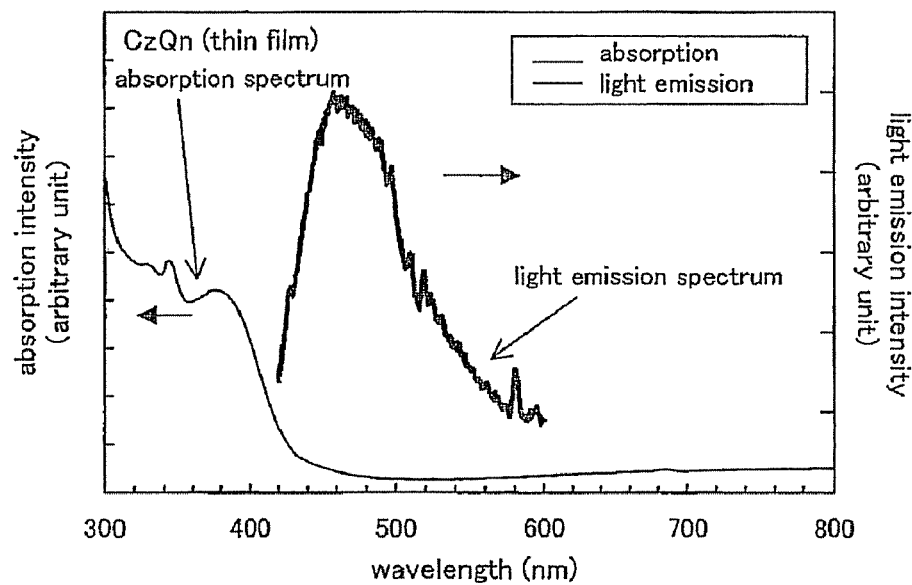

An absorption-light emission spectrum of CzQn in a toluene solution is shown in FIG. 5(a), and an absorption-light emission spectrum of a thin film is shown in FIG. 5(b). In the solution, a purple-blue light emission having a peak at 440 nm was obtained, and, in the thin film state, a blue light emission having a peak at 460 nm was obtained. Also a HOMO level in a thin film state, measured by a photoelectron spectroscopy (AC-2, manufactured by Riken Keiki Co.) in the air, was −5.94 eV. Also, taking an absorption end of the absorption spectrum shown in FIG. 5(b) as an energy gap, a LUMO level was −3.02 eV.

Synthesis Example 3

A quinoxaline derivative of the present invention represented by the foregoing structural formula (50) (hereinafter represented as PoxQn) can be obtained by employing phenoxazine instead of diphenylamine in the synthesis example 1.

The obtained PoxQn had a decomposition temperature of 434° C. and was easily capable of film formation by a vacuum evaporation method by a resistance heating. A uniform film was formed without crystallization, coagulation or the like.

A light emission spectrum of PoxQn in a toluene solution had a peak at 556 nm and in a thin film state had a peak at 561 nm, both green-yellow light emission. Measurements of a HOMO level and a LUMO level in a thin film state in a method similar to that in the synthesis example 1 provided a HOMO level of −5.59 eV and a LUMO level of −3.11 eV.

Synthesis Example 4

A quinoxaline derivative of the present invention represented by the foregoing structural formula (56) (hereinafter represented as PthQn) can be obtained by employing phenothiazine instead of diphenylamine in the synthesis example 1.

The obtained PthQn had a decomposition temperature of 428° C. and was easily capable of film formation by a vacuum evaporation method by a resistance heating. A uniform film was formed without crystallization, coagulation or the like.

A light emission spectrum of PthQn in a toluene solution was a yellow light emission having a peak at 575 nm and in a thin film state was a green-yellow light emission having a peak at 554 nm. Measurements of a HOMO level and a LUMO level in a thin film state in a method similar to that in the synthesis example 1 provided a HOMO level of −5.53 eV and a LUMO level of −2.81 eV.

Synthesis Example 5

A quinoxaline derivative of the present invention represented by the foregoing structural formula (27) (hereinafter represented as NPADiBzQn) can be obtained by employing 9,10-phenanthrenediamine instead of o-phenylenediamine and N-(1-naphthyl)-N-phenylamine instead of diphenylamine in the synthesis example 1.

The obtained NPADiBzQn had a decomposition temperature of 460° C. and was easily capable of film formation by a vacuum evaporation method by a resistance heating. A uniform film was formed without crystallization, coagulation or the like.

A light emission spectrum of NPADiBzQn in a toluene solution was a blue light emission having a peak at 469 nm and in a thin film state was a blue-green light emission having a peak at 490 nm. Measurements of a HOMO level and a LUMO level in a thin film state in a method similar to that in the synthesis example 1 provided a HOMO level of −5.55 eV and a LUMO level of −2.91 eV.

Embodiment 2

This embodiment provides a specific example of an electric field light emitting device employing a light emitting layer constituted solely of the quinoxaline derivative (TPAQn) of the present invention obtained in the foregoing synthesis example 1. The device structure was made similar to that shown in FIG. 1.

At first, there was employed a substrate 100 in which an ITO film of 110 nm was formed as a first electrode 101 on a glass. The ITO was so formed as to function in an electrode of a size of 2 mm square. The ITO functions as an anode.

Then films of CuPc of 20 nm as a hole injecting layer 111, α-NPD of 30 nm as a hole transporting layer 112 and TPAQn of 30 nm as a light emitting layer 113 were formed. Further, BCP of 20 nm and Alq of 20 nm were laminated in succession as an electron transporting layer 114. Further, in the present embodiment, after calcium fluoride of 2 nm as a layer for promoting electron injection was laminated on the electron transporting layer 114, aluminum (Al) of 100 nm was laminated as a second electrode 103 to obtain an organic semiconductor device (electric field light emitting device) of the present invention.

Figure 6:
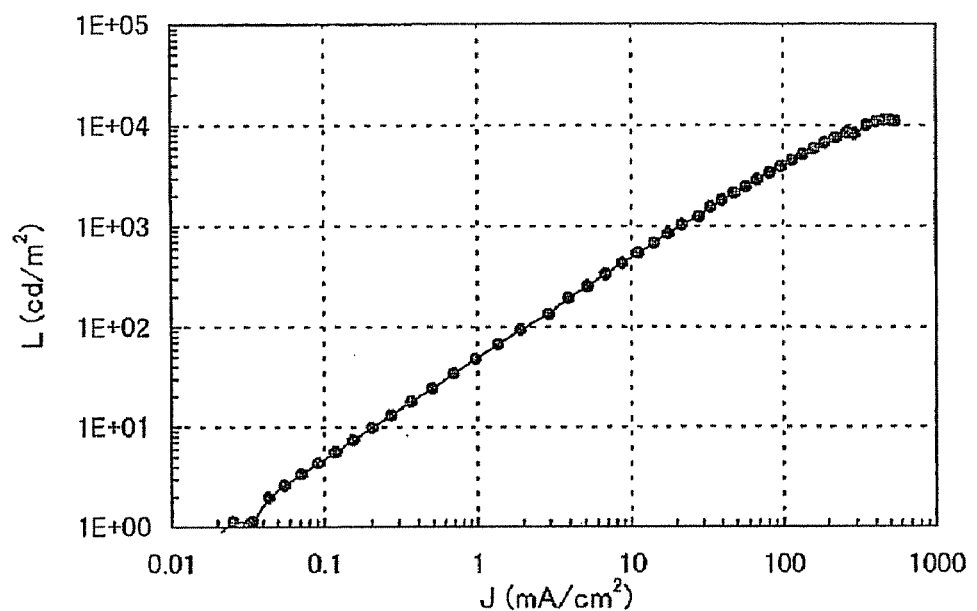
FIG. 6 is a view showing luminance-current density (L-J) characteristics of the electric field light emitting device of the present invention.
Figure 7:
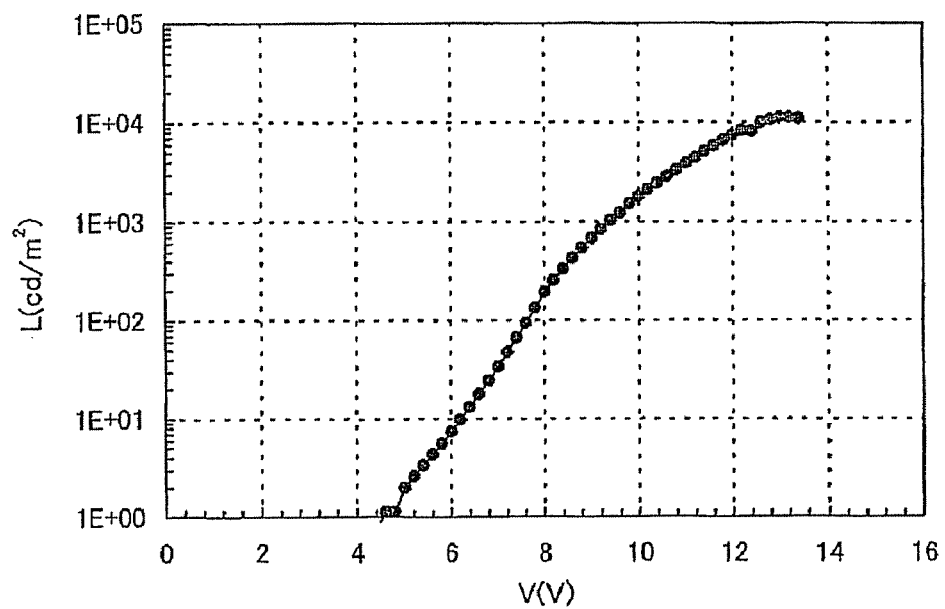
FIG. 7 is a view showing luminance-voltage (L-V) characteristics of the electric field light emitting device of the present invention.

Luminance-current density (L-J) characteristics and luminance-voltage (L-V) characteristics of the obtained device are respectively shown in FIGS. 6 and 7. This device, under an application of a voltage of 9.4 V, showed a current of a current density of 21.9 mA/cm$^2$ and a light emission at a luminance of 1030 cd/m$^2$. A current efficiency was 4.71 cd/A.

Figure 8:
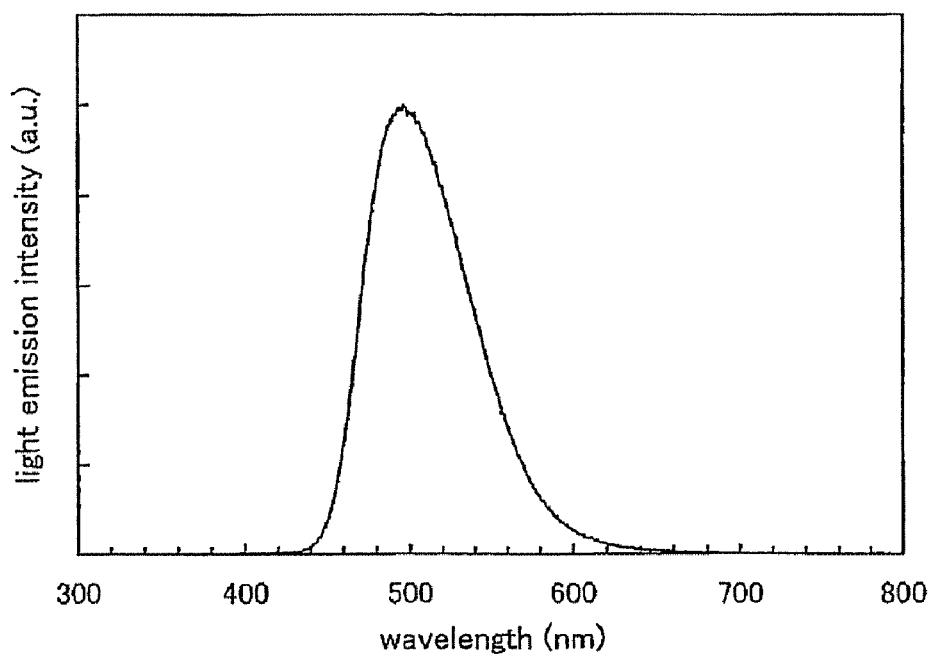
FIG. 8 is a view showing a light emission spectrum of the electric field light emitting device of the present invention.

Also a light emission spectrum of this device is shown in FIG. 8. As shown in FIG. 8, there was obtained a blue-green light emission having a maximum peak value at about 500 nm.

Embodiment 3

This embodiment provides a specific example of an electric field light emitting device employing a quinoxaline derivative (TPAQn) of the present invention obtained in the foregoing synthesis example 1 as a guest material of the light emitting layer. The device structure was made similar to that shown in FIG. 1, but materials for forming the layers were made different from those in Embodiment 1.

At first, there was employed a substrate 100 in which an ITO film of 110 nm was formed as a first electrode 101 on a glass. The ITO was so formed as to function in an electrode of a size of 2 mm square. The ITO functions as an anode.

Then films of CuPc of 20 nm as a hole injecting layer 111, and α-NPD of 30 nm as a hole transporting layer 112 were formed. Then a light emitting layer 113 of 30 nm was formed by co-evaporating DNA and TPAQn so as to obtain a weight ratio of 4:0.3 (namely TPAQn constituted about 7 wt. %). Further, BCP of 20 nm was formed as an electron transporting layer 114, then calcium fluoride of 2 nm as a layer for promoting electron injection was laminated on the electron transporting layer 114, and aluminum (Al) of 100 nm was laminated as a second electrode 103 to obtain an organic semiconductor device (electric field light emitting device) of the present invention.

Figure 9:
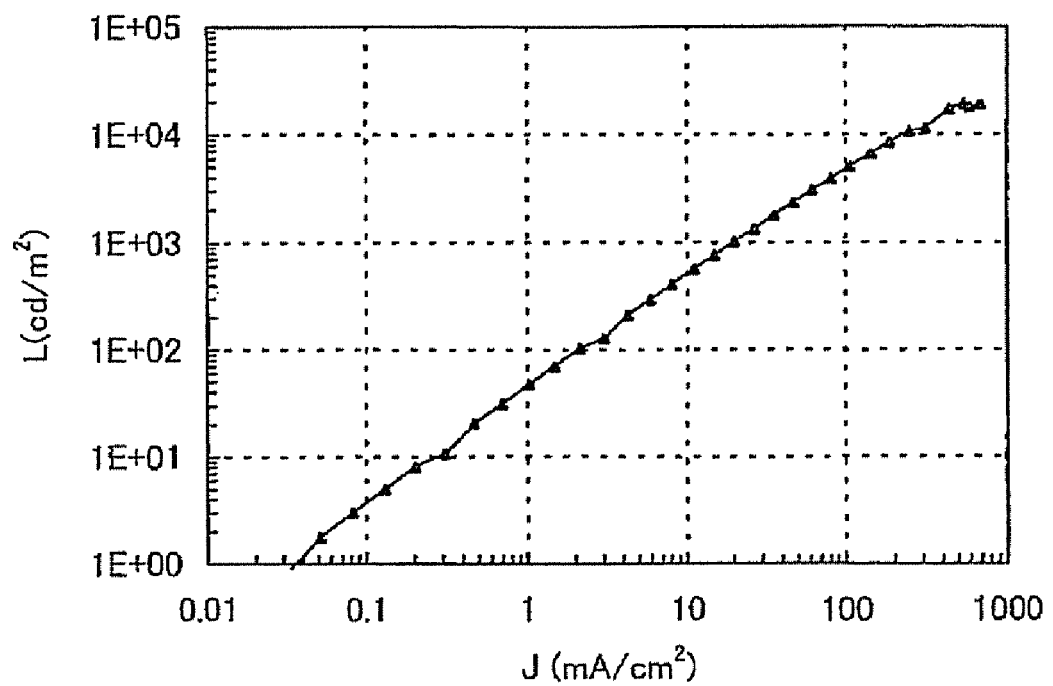
FIG. 9 is a view showing luminance-current density (L-J) characteristics of the electric field light emitting device of the present invention.
Figure 10:
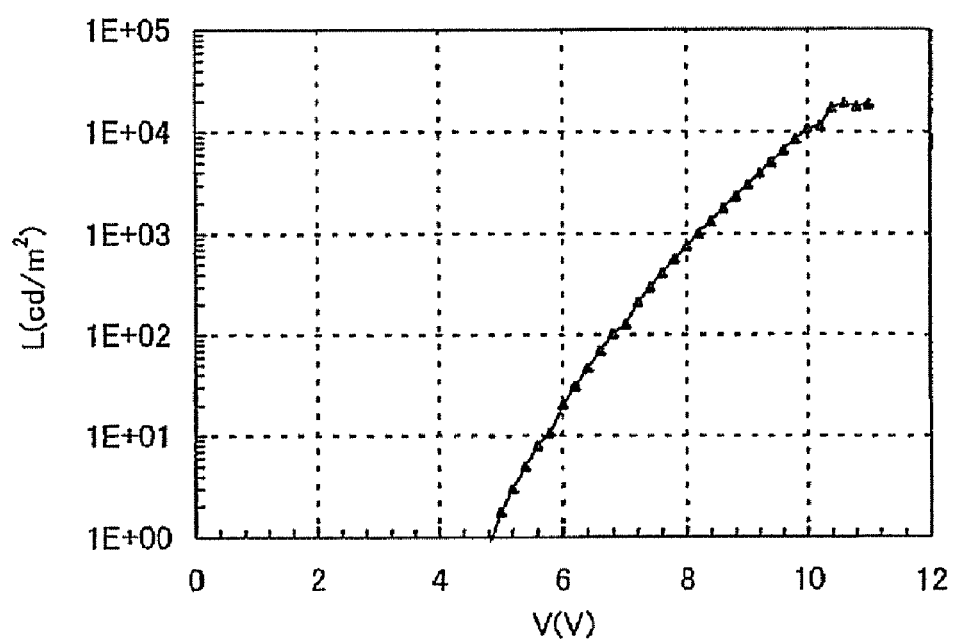
FIG. 10 is a view showing luminance-voltage (L-V) characteristics of the electric field light emitting device of the present invention.

Luminance-current density (L-J) characteristics and luminance-voltage (L-V) characteristics of the obtained device are respectively shown in FIGS. 9 and 10. This device, under an application of a voltage of 8.2 V, showed a current of a current density of 20.2 mA/cm$^2$ and a light emission at a luminance of 1025 cd/m$^2$. A current efficiency was 5.08 cd/A.

Figure 11:
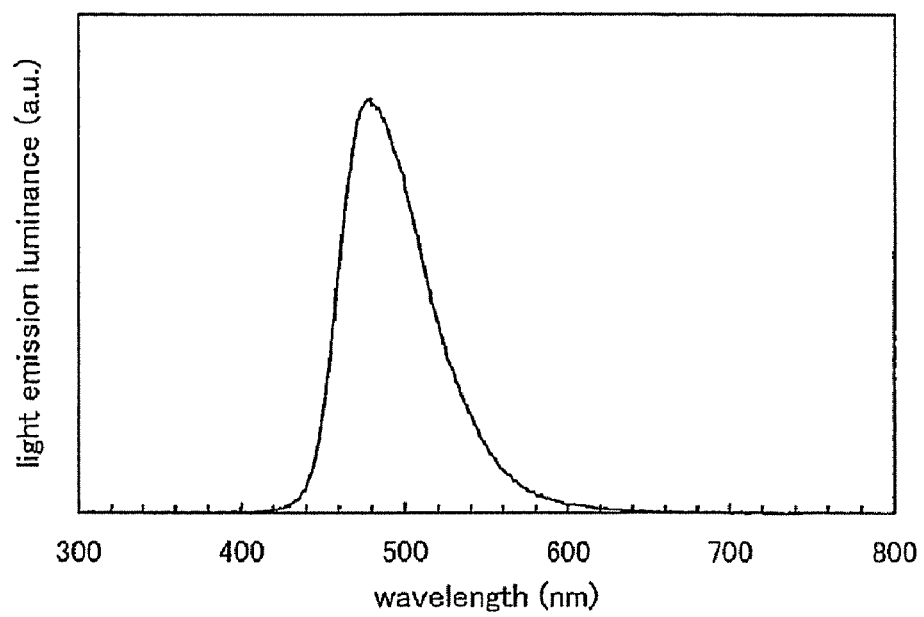
FIG. 11 is a view showing a light emission spectrum of the electric field light emitting device of the present invention.

Also a light emission spectrum of this device is shown in FIG. 11. As shown in FIG. 11, there was obtained a blue light emission having a maximum peak value at about 480 nm.

Embodiment 4

This embodiment provides a specific example of an electric field light emitting device employing a quinoxaline derivative (TPAQn) of the present invention obtained in the foregoing synthesis example 1 as a host material of the light emitting layer. There is particularly shown an example of a device utilizing a phosphorescent material showing a light emission from a triplet excited state. The device structure was made similar to that shown in FIG. 1, but materials for forming the layers were made different from those in Embodiment 1.

At first, there was employed a substrate 100 in which an ITO film of 110 nm was formed as a first electrode 101 on a glass. The ITO was so formed as to function in an electrode of a size of 2 mm square. The ITO functions as an anode.

Then films of CuPc of 20 nm as a hole injecting layer 111, and α-NPD of 30 nm as a hole transporting layer 112 were formed. Then a light emitting layer 113 of 30 nm was formed by co-evaporating TPAQn and Ir(btp)$_2$(acac) in such a manner that Ir(btp)$_2$(acac) was contained by about 8.8 wt. %. Further, BCP of 10 nm and Alq of 20 nm were laminated in succession as an electron transporting layer 114. Also calcium fluoride of 2 nm as a layer for promoting electron injection was laminated on the electron transporting layer 114, and aluminum (Al) of 100 nm was laminated as a second electrode 103 to obtain an organic semiconductor device (electric field light emitting device) of the present invention.

Figure 12:
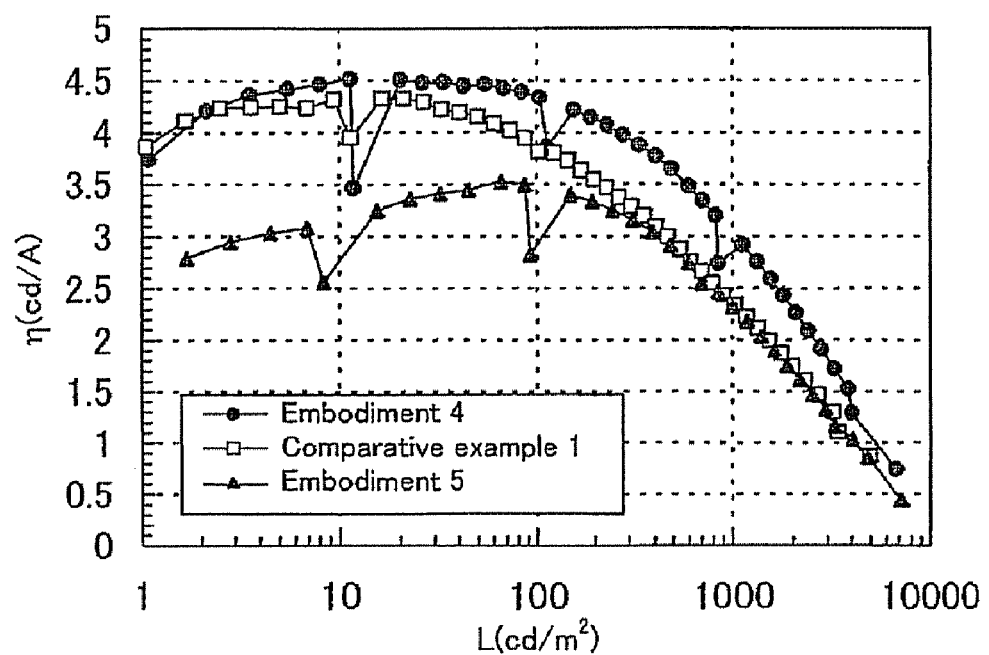
FIG. 12 is a view showing current efficiency-luminance (η-L) characteristics of the electric field light emitting device of the present invention.
Figure 13:
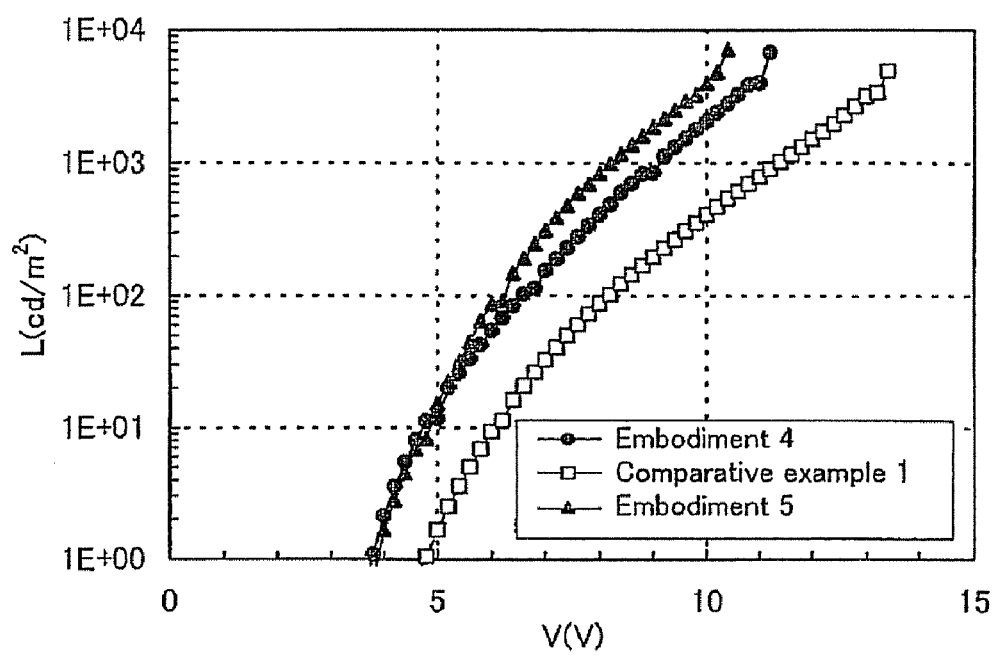
FIG. 13 is a view showing luminance-voltage (L-V) characteristics of the electric field light emitting device of the present invention.

Current efficiency-luminance (η-L) characteristics and luminance-voltage (L-V) characteristics of the obtained device are respectively indicated by "Embodiment 4" in FIGS. 12 and 13. This device had a drive voltage of 7.2 V at a light emission with a luminance of about 200 cd/m$^2$, with a current of a current density of 4.58 mA/cm$^2$. A current efficiency was 4.14 cd/A.

Figure 14:
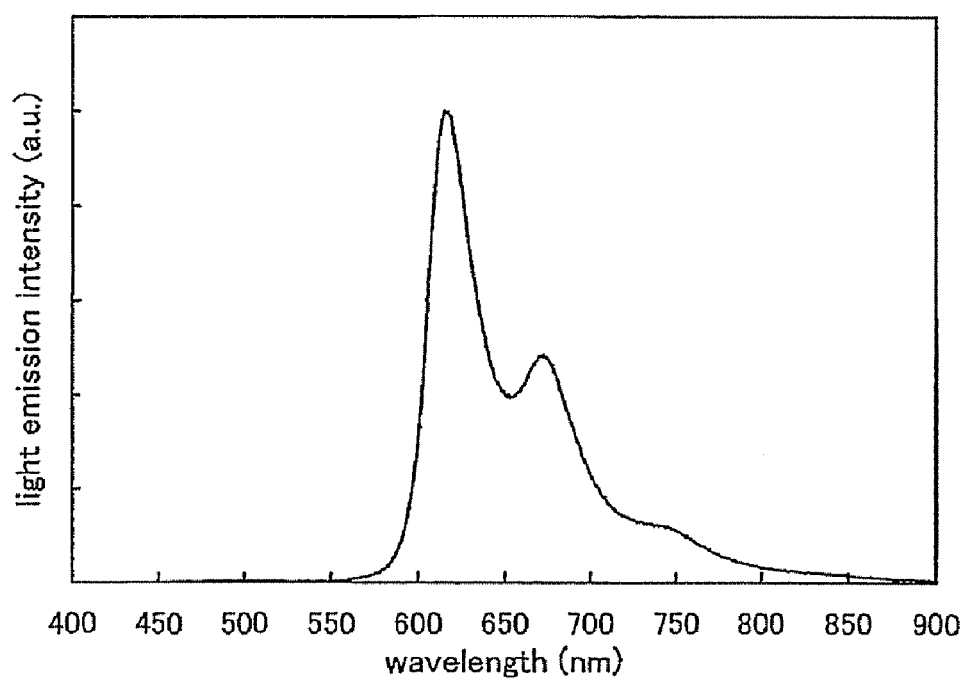
FIG. 14 is a view showing a light emission spectrum of the electric field light emitting device of the present invention.

Also a light emission spectrum of this device is shown in FIG. 14. Based on the shape of the spectrum, the light emission was identified from the phosphorescent material Ir(btp)$_2$(acac). The CIE chromaticity coordinates were (x, y)=(0.31, 0.69), and it was a red light emission with satisfactory chromaticity.

As explained in the foregoing, the current efficiency was 4.14 cd/A at 200 cd/m$^2$, and there was realized a device of a very high efficiency as a red light emitting device. Such high efficiency is a feature of the device utilizing a phosphorescent material, and the device of the present embodiment fully exploits such feature. Therefore, the quinoxaline derivative of the present invention is suitable as a host material in a light emitting layer utilizing a phosphorescent material.

Comparative Example 1

For the purpose of comparison with Embodiment 4, there is shown an example of characteristics of a conventional electric field light emitting device employing Ir(btp)$_2$(acac) as a guest. The device structure was similar to Embodiment 4, except for the light emitting layer 113. The light emitting layer 113 had a conventional structure with CBP as a host, and an addition concentration of Ir(btp)$_2$(acac) was selected as about 7.5 wt %.

Current efficiency-luminance (η-L) characteristics and luminance-voltage (L-V) characteristics of the obtained device are respectively indicated by "Comparative example 1" in FIGS. 12 and 13. This device had a drive voltage of 9.0 V at a light emission with a luminance of about 200 cd/m$^2$, with a current of a current density of 5.55 mA/cm$^2$. A current efficiency was 3.55 cd/A.

Also a light emission spectrum of this device was about same as in FIG. 14. The CIE chromaticity coordinates were (x, y)=(0.31, 0.67).

In comparison with Embodiment 4, the light emission spectrum and the chromaticity were about same, but the current efficiency was somewhat inferior (FIG. 12). Thus, the quinoxaline derivative of the present invention proved to be more suitable material than the conventional material, as a host material of the light emitting layer.

Also this comparative example 1 had a higher drive voltage in comparison with Embodiment 4 (FIG. 13). For example the drive voltage for attaining about 200 cd/m$^2$ was 9.0 V which was higher by 1.8 V than in Embodiment 4 (7.2 V). Therefore the use of the quinoxaline derivative of the present invention as the host material enabled to reduce the drive voltage than in the conventional art.

Figure 15:
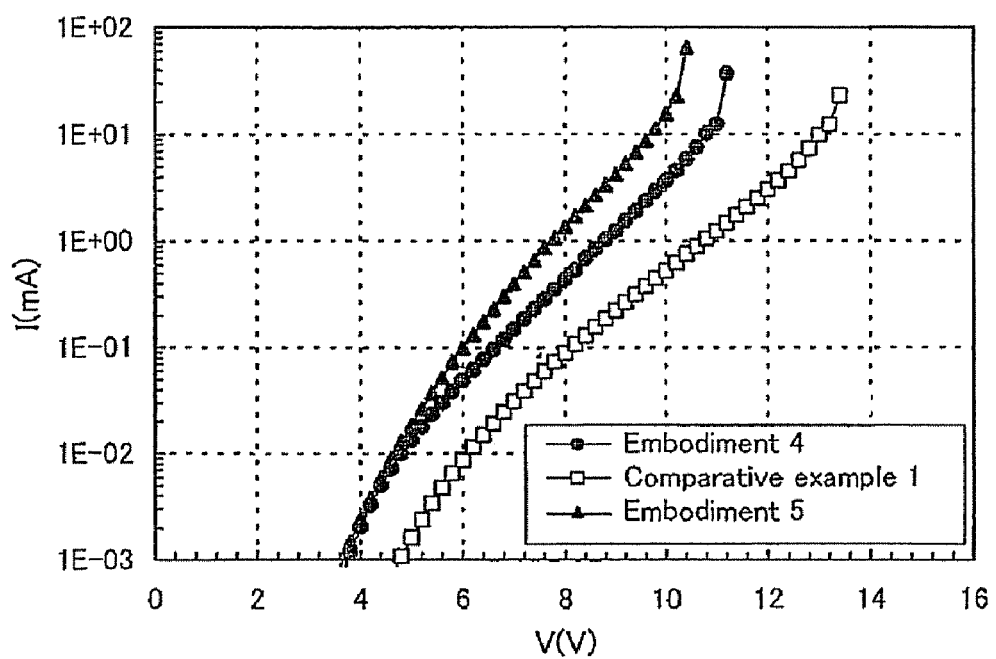
FIG. 15 is a view showing current-voltage (I-V) characteristics of the electric field light emitting device of the present invention.

FIG. 15 shows current-voltage (I-V) characteristics of Embodiment 4 and Comparative example 1. Embodiment 4 shows an apparent shift to a lower voltage side, indicating a higher current flowability. This fact indicates that the quinoxaline derivative of the present invention is superior to CBP in the carrier transporting property, thus contributing to a decrease in the drive voltage. Thus, the quinoxaline derivative of the present invention, having an excellent carrier transporting property, can be considered to similarly decrease the drive voltage also in case of being employed as a host material for other various light emitting materials.

Based on the foregoing, it was identified that the use of the quinoxaline derivative of the present invention as the host material in the light emitting layer could reduce the drive voltage. It was particularly identified, in the use as the host material of the phosphorescent material, that an electric field light emitting device could be realized with a higher efficiency and a lower drive voltage than in the conventional art.

Embodiment 5

This embodiment provides a specific example of an electric field light emitting device employing a quinoxaline derivative (TPAQn) of the present invention obtained in the foregoing synthesis example 1 as a host material of the light emitting layer. There is particularly shown an example of a device utilizing a phosphorescent material showing a light emission from a triplet excited state as a guest. The device structure was made same as in Embodiment 4, except that BCP was eliminated therefrom.

At first, there was employed a substrate 100 in which an ITO film of 110 nm was formed as a first electrode 101 on a glass. The ITO was so formed as to function in an electrode of a size of 2 mm square. The ITO functions as an anode.

Then films of CuPc of 20 nm as a hole injecting layer 111, and α-NPD of 40 nm as a hole transporting layer 112 were formed. Then a light emitting layer 113 of 30 nm was formed by co-evaporating TPAQn and Ir(btp)$_2$(acac) in such a manner that Ir(btp)$_2$(acac) was contained by about 1.0 wt. %. Further, Alq of 20 nm was laminated as an electron transporting layer 114. Also calcium fluoride of 2 nm as a layer for promoting electron injection was laminated on the electron transporting layer 114, and aluminum (Al) of 100 nm was laminated as a second electrode 103 to obtain an organic semiconductor device (electric field light emitting device) of the present invention.

Current efficiency-luminance (η-L) characteristics and luminance-voltage (L-V) characteristics of the obtained device are respectively indicated by "Embodiment 5" in FIGS. 12 and 13. This device had a drive voltage of 6.6 V at a light emission with a luminance of about 200 cd/m$^2$, with a current of a current density of 5.79 mA/cm$^2$. A current efficiency was 3.44 cd/A.

Also a light emission spectrum of this device was similar to the spectrum shown in FIG. 14. The CIE chromaticity coordinates were (x, y)=(0.32, 0.68), and it was a red light emission with satisfactory chromaticity.

The current efficiency was similar to the conventional art (Comparative example 1), and there was realized a device of a very high efficiency as a red light emitting device (FIG. 12). Also from FIG. 13 it can be understood that the drive voltage is very low in comparison with Comparative example 1. For example, the drive voltage for attaining about 200 cd/m$^2$ was 6.6 V which was lower by as much as 2.4 V in comparison with 9.0 V in Comparative example 1. The I-V characteristics shown in "Embodiment 5" in FIG. 15 also shows a shift to a lower voltage side in comparison with the conventional art (Comparative example 1), and the high carrier transporting property of the quinoxaline derivative of the present invention is considered to contribute to the decrease in the drive voltage.

It is particularly to be noted that a highly efficient device is realized without utilizing BCP which is applied in the electron transporting layer of Embodiment 4 and Comparative example 1. In a device causing light emission of a phosphorescent material, it has normally been considered necessary to provide, next to the light emitting layer, an electron transporting layer (so-called hole blocking layer) constituted of a material capable of enclosing holes or excitons, namely a hole blocking material or an exciton blocking material, such as BCP in Embodiment 4 or Comparative example 1. This is because, without such layer, the excitation energy of the phosphorescent material is transferred to the ordinarily employed material of the electron transporting layer such as Alq, so that an efficient light emission cannot be obtained from the phosphorescent material.

However, according to present Embodiment 5, in case of employing the quinoxaline derivative of the present invention as the host material to the phosphorescent material, it is unnecessary to provide so-called hole blocking layer and made possible to decrease the number of layers. Also a hole blocking material or an exciton blocking material such as BCP generally shows a severe crystallization and results in a deterioration of reliability, so that the result of Embodiment 5 allowing to dispense with such materials leads to an advantage of an improvement in the reliability of the electric field light emitting device utilizing the phosphorescent material.

Furthermore, the result of Embodiment 5 indicates that the efficiency of the energy transfer from the quinoxaline derivative of the present invention to the phosphorescent material is extremely satisfactory. Also in this sense, the quinoxaline derivative of the present invention is suitable as a host material for the light emitting layer employing the phosphorescent material.

The invention claimed is:

1. A quinoxaline derivative represented by a structural formula (14).

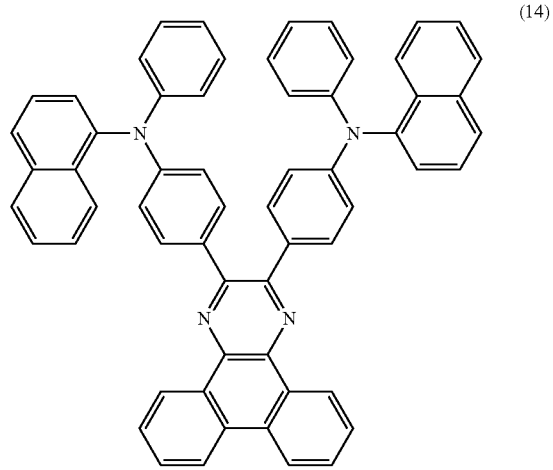

2. An electric field light emitting device comprising a quinoxaline derivative represented by a structural formula (14) between a pair of electrodes.

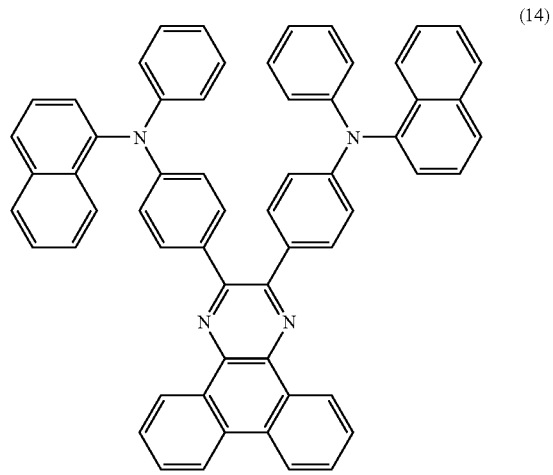

3. A host material including the quinoxaline derivative according to claim 1.

4. An organic semiconductor device, wherein the quinoxaline derivative according to claim 1 is included in an active layer.

5. An electronic device comprising the organic semiconductor device according to claim 4.

6. An electronic device according to claim 5, wherein the electronic device is any one of a personal computer, a portable telephone and a television receiver.

7. An electric field light emitting device comprising a light emitting layer containing a quinoxaline derivative represented by a structural formula (14) and a phosphorescent material showing a light emission from a triplet excited state between a pair of electrodes.

8. An electric field light emitting device according to claim 7, wherein a light emission spectrum of the phosphorescent material has a peak from 560 to 700 nm.

9. An electronic device employing the electric field light emitting device according to claim 7.

10. An electronic device according to claim 9, wherein the electronic device is any one of a personal computer, a portable telephone and a television receiver.

11. An illuminating apparatus comprising a quinoxaline derivative represented by a structural formula (14) between a pair of electrodes.

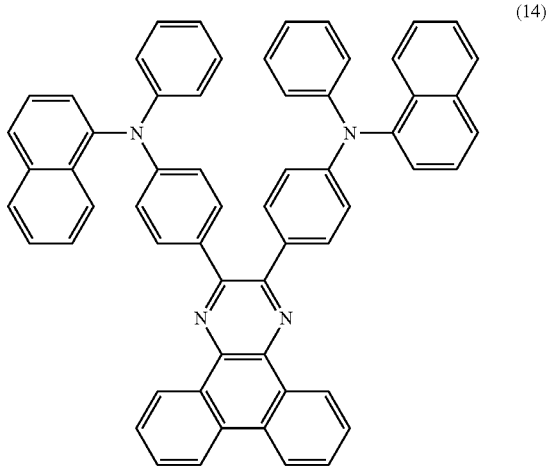

(14)

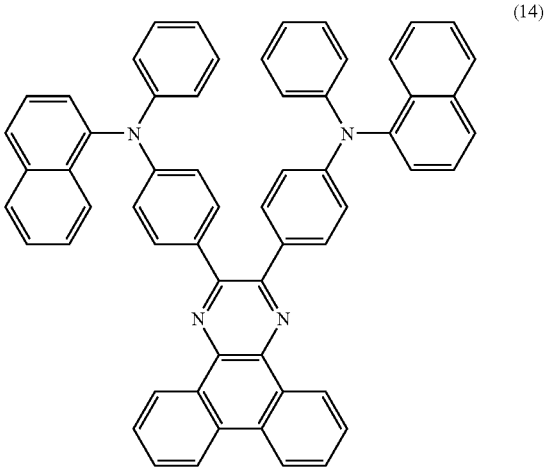

(14)

* * * * *